United States Patent [19]

Harrison et al.

[11] Patent Number: 5,268,389
[45] Date of Patent: Dec. 7, 1993

[54] THIOCARBOXYLATE ESTER COMPOUNDS COMPOSITIONS CONTAINING THE SAME

[75] Inventors: William A. Harrison; Ethel E. Felauer; Walter G. Brouwer, all of Guelph, Canada

[73] Assignees: Uniroyal Chemical Company, Inc., Middlebury, Conn.; Uniroyal Chemical Ltd./Ltee, Elmira, Canada

[21] Appl. No.: 588,208

[22] Filed: Sep. 26, 1990

Related U.S. Application Data

[63] Continuation-in-part of Ser. No. 567,982, Aug. 15, 1990, abandoned, which is a continuation-in-part of Ser. No. 421,155, Oct. 16, 1989, abandoned.

[51] Int. Cl.$^5$ .................. A61K 31/265; C07C 333/08
[52] U.S. Cl. ...................................... 514/485; 558/234
[58] Field of Search ................. 558/230, 234; 514/485

[56] References Cited

U.S. PATENT DOCUMENTS

| | | | |
|---|---|---|---|
| 4,861,759 | 8/1989 | Mitsuya et al. | 514/46 |
| 4,880,782 | 11/1989 | Eckstein et al. | 514/45 |
| 4,971,977 | 11/1990 | Turano | 514/307 |
| 4,980,371 | 12/1990 | Parker et al. | 514/461 |

FOREIGN PATENT DOCUMENTS 0104070 9/1983 European Pat. Off. .

OTHER PUBLICATIONS

*Chemical Abstracts* vol. 101, No. 13, Sep. 24, 1984, Abstract No. 110567b.

*Primary Examiner*—Mary C. Lee
*Assistant Examiner*—Jacqueline Haley
*Attorney, Agent, or Firm*—Glenn E. Karta

[57] ABSTRACT

A method of inhibiting the growth or replication of viruses of the HIV group is disclosed. Also disclosed are compounds useful in the method and pharmaceutical formulations incorporating such compounds. The method involves the use of compounds having the general formula:

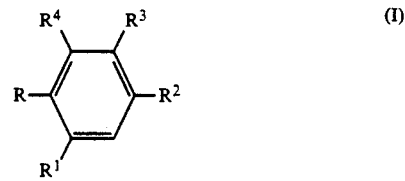

(I)

wherein the substituent groups are as defined in the specification.

8 Claims, 2 Drawing Sheets

THIOCARBOXYLATE ESTER COMPOUNDS COMPOSITIONS CONTAINING THE SAME

This is a Continuation-In-Part of U.S. Ser. No. 567,982 filed Aug. 15, 1990 now abandoned, which is a Continuation-In-Part of U.S. Ser. No. 421,155 filed 16 October, 1989, now abandoned.

BACKGROUND OF THE INVENTION

1. Field of the Invention

This invention relates to treatment for inhibiting the growth or replication of viruses of the Human Immunodeficiency Virus (HIV) group, to compounds useful therein, and to pharmaceutical formulations incorporating such compounds.

2. Background of the Invention

Viruses are the smallest known infectious agents. They are made up of a nucleic acid (either Deoxyribonucleic Acid (DNA) or Ribonucleic Acid (RNA)) and viral proteins which are encased in a protein shell.

Viral infections, as a group, are among the most difficult infections to treat because of the way viruses replicate and interact with the cells which they infect. Thus current methods of treatment directed towards preventing the growth or replication of viruses often result in some degree of disturbance to the host cell's metabolism, with resultant toxicity to the host cells.

Generally, viruses first bind to the outer membrane of a particular host cell. After binding occurs, the viral nucleic acids (DNA or RNA) along with selected viral proteins enter into the host cell.

The viral nucleic acids then take over the metabolic machinery of the host cell and force the host cell to produce viral nucleic acid and proteins, which then assemble and are eventually released from the cell. Since release of the virus causes the cell membrane to rupture, a completed viral replication cycle results in the death of the host cell.

Viruses are generally divided into DNA or RNA viruses (depending on the type of nucleic acid they contain) and are further subdivided into various families.

Retroviruses are RNA viruses which contain high molecular weight RNA, traces of DNA, and various enzymes, including reverse transcriptase and nucleases enclosed by a protein coating. This type of virus first binds to the outer membrane of an appropriate cell, followed by injection of viral RNA and reverse transcriptase into the host cell.

Reverse transcriptase uses the viral RNA as a template to produce a complimentary DNA strand. This DNA becomes incorporated into the host's DNA and causes the host cell to produce viral RNA and viral proteins.

A subgroup of viruses in the Retrovirus family comprises human immunodeficiency viruses (HIV) which are known to preferentially attack cells of the human immune and nervous systems. HIV-I is the designation of the virus that is one of the etiologic agents for the development of Acquired Immune Deficiency Syndrome ("AIDS") in humans. It is known that HIV is transmitted by the exchange of bodily fluids, such as sexual secretions and blood, e.g., as a result of sexual contact, transfusions, or sharing of needles, for instance by intravenous drug users.

The HIV group infects and destroys the CD-4-T-lymphocytes (helper T-lymphocytes) and cells of the central nervous system.

Helper-T lymphocytes are vital to the immune system and are necessary for the immune system to be able to fight off opportunistic organisms such as pneumocystis carinii (which causes pneumonia), Toxoplasma gondii (Toxoplasmosis), viral infections caused by Herpes and Varicella viruses and also to prevent the formation of certain cancers, the most notable being Kaposi's Sarcoma.

Loss of these cells by HIV infection, either quantitatively or functionally, eventually leads to the loss of ability of the human immune system to fight off these diseases. Helper T-lymphocytes are also needed to fight HIV infection. It is the loss of helper T-cells which results in the severe immune deficiency that is one characteristic of AIDS. HIV infections of the central nervous system result in progressive loss of cerebral function, which culminates in AIDS dementia complex.

As of this date, AIDS caused by HIV has reached epidemic proportions in various parts of the world, including the United States.

Various known antiviral drugs have been tested for the prevention or treatment of HIV infections including alpha interferon, gamma interferon, azimexon, isopinosine, and Azidothymidine (or AZT). To date, the only substance which has achieved some clinical success is AZT. This substance is a synthetic thymidine analog that is incorporated into DNA and causes the premature termination of the synthesis of DNA. This results in the inhibition of viral replication, since DNA needed to produce the viral RNA is not produced.

However, DNA synthesis is also necessary for the continued normal functioning of the host cell. Consequently, administration of AZT results in the inhibition of host DNA synthesis with concomitant severe side effects, e.g., anemia, granulocytopenia, and thrombocytopenia.

Thus, there is a continuing need for better anti-HIV treatments and for better anti-HIV drugs.

SUMMARY OF THE INVENTION

Treatments and drugs that satisfy this need have now been developed.

In accordance with one aspect of the present invention, a method for inhibiting the growth or replication of HIV is provided, which comprises administering an effective amount of a compound having the formula I:

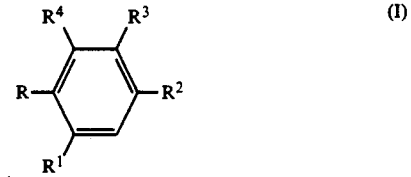

(I)

wherein:

$R^1$ is hydrogen, halogen, $C_1$-$C_4$ alkyl or $C_1$-$C_4$ alkoxy;

$R^2$ is hydrogen, halogen, $C_1$-$C_4$ alkyl, $C_1$-$C_4$ alkoxy, mono-, di- or tri-halomethyl, trifluoromethoxy, methylthio, nitro, cyano, acetoxy or dimethylamino;

$R^3$ is i) $-SO_2NR^aR^b$, ii) $CO_2R^5$, iii) $-(CH_2)_{n3}-Y-R^d$, iv) $-G-CO_2R^5$, v) $-CH=NOR^a$, vi) $-CS_2R^5$, vii) $-COSR^5$, viii) $-O(CH_2)_n-P(O)(OR^a)(OR^b)$, ix) $-COR^a$ or

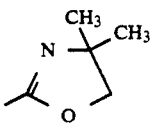

x)

$R^4$ is hydrogen, halogen, methyl or mono-, di- or tri-halomethyl; and
R is

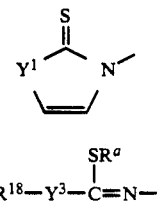

i)

ii)

or $R^z$—NH—  iv)

wherein the substituent groups are defined in more detail in the Detailed Description.

DETAILED DESCRIPTION OF THE EMBODIMENTS

Figure 1:
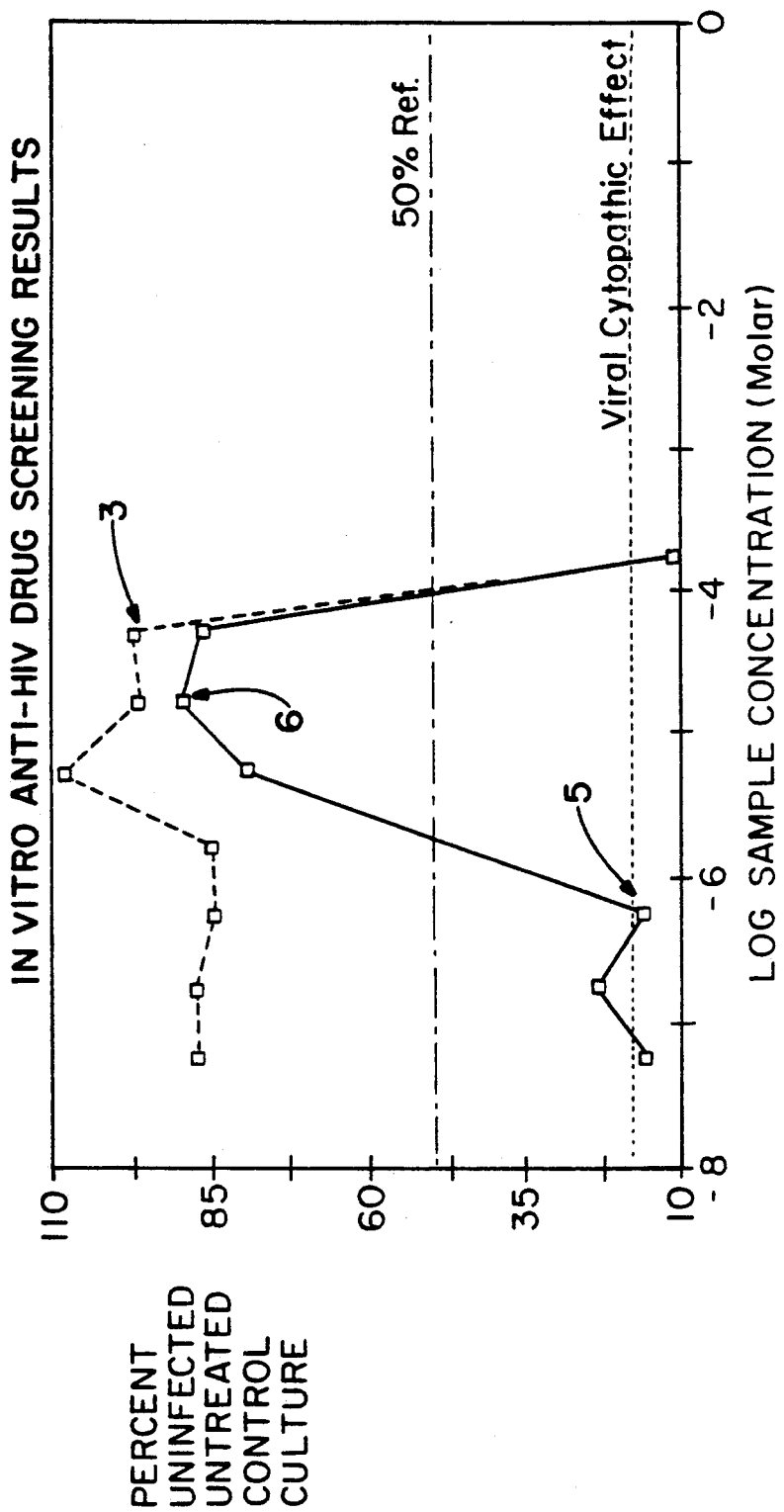
FIG. 1 is a graph illustrating inhibition of the viral cytopathic effect of HIV-I with increasing concentration of the compound of Example 1 below.

The compounds useful in the treatment of this invention are compounds of the formula:

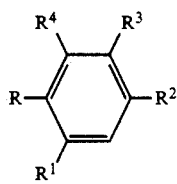

(I)

wherein:
$R^1$ is hydrogen, halogen, $C_1$-$C_4$ alkyl or $C_1$-$C_4$ alkoxy;
$R^2$ is hydrogen, halogen, $C_1$-$C_4$ alkyl, $C_1$-$C_4$ alkoxy, hydroxy, mono-, di- or tri-halomethyl, trifluoromethoxy, methylthio, nitro, cyano, acetoxy or dimethylamino;
$R^3$ is
  i) —$SO_2NR^aR^b$ wherein $R^a$ and $R^b$ are independently hydrogen or $C_1$-$C_6$ alkyl or together form a heterocycle wherein the heterocyclic moiety is morpholinyl, piperidinyl, pyrrolidinyl or piperazinyl;
  ii) —$CO_2R^5$ wherein
    $R^5$ is an alkyl, a $C_3$-$C_6$ alkenyl or alkynyl, a one to six haloalkyl, an alkoxyalkyl, an alkylthioalkyl, a carboxyalkyl, an alkylcarboxyalkyl, a $C_6$-$C_{12}$ arylcarboxyalkyl, an alkylaminoalkyl or dialkylaminoalkyl, a trialkylsilylalkyl, each of the aforementioned alkyl moieties having from one to eight carbon atoms; a phenyl, a naphthyl, a $C_1$-$C_6$ alkylphenyl, a $C_7$-$C_{12}$ arylalkyl or alkarylalkyl, a $C_3$-$C_8$ carbocyclyl, a $C_1$-$C_4$ alkyl $C_3$-$C_8$ carbocyclyl, or a heterocyclylalkyl, wherein the hetero cyclic moiety is morpholinyl, piperidinyl, pyrrolidinyl, piperazinyl, oxiranyl, oxetanyl, furanyl or tetrahydrofuranyl;
  iii) —$(CH_2)_{n3}$—Y—$R^d$ wherein
    $n^3$ is 0 or 1;
    Y is O, S, SO, $SO_2$ or NH; and
    $R^d$ is $C_1$-$C_6$ alkyl, $C_3$-$C_6$ cycloalkyl, $C_2$-$C_6$ alkenyl, $C_2$-$C_6$ alkynyl, —$CH_2CO_2R^5$, —$CO_2R^5$ with the proviso that Y cannot be $SO_2$, or —$COR^a$ wherein
    $R^5$ and $R^a$ are as defined above;
  iv) —G—$CO_2R^5$ wherein
    G is —$CH_2$—, —$CH_2CH_2$— or —CH=CH—, and
    $R^5$ is as defined above;
  v) —CH=$NOR^a$ wherein $R^a$ is as defined above;
  vi) —$CS_2R^5$ wherein $R^5$ is as defined above;
  vii) —$COSR^5$ wherein $R^5$ is as defined above;

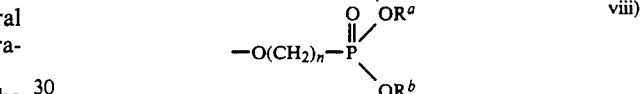

viii)

n is 1 or 2,
$R^a$ and $R^b$ are independently hydrogen or $C_1$-$C_6$ alkyl;
ix) —$COR^a$ wherein $R^a$ is defined above; or

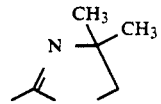

x)

$R^4$ is hydrogen, halo, methyl or mono-, di- or tri-halomethyl;
R is

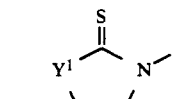

i)

wherein
$Y^1$ is O, S, NH or $NR^a$ wherein $R^a$ is as defined above;

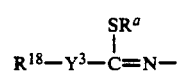

ii)

wherein
$R^{18}$ is linear or branched $C_1$-$C_6$ alkyl or alkoxyalkyl wherein the alkyl groups are $C_1$-$C_6$, $C_3$-$C_8$ cycloalkyl or mono-, di- or tri-halo $C_1$-$C_6$ alkyl;
$Y^3$ is O or S; and
$R^a$ is as defined above; or
iii) $R^z$—NH— wherein $R^z$ is

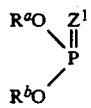
a)

wherein
$R^a$ and $R^b$ are independently hydrogen or $C_1$-$C_6$ alkyl; and
$Z^1$ is O or S;
b) cyano;

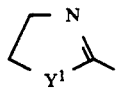
c)

wherein
$Y^1$ is as defined above; or

d)

wherein
$Z^2$ is O, S, NH, $NR^a$ or $NC\equiv N$; wherein
$R^a$ is as defined above; and
$R^A$ is

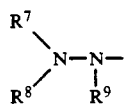
1)

wherein
$R^7$, $R^8$ and $R^9$ are independently hydrogen or $C_1$-$C_6$ alkyl, or $R^7$ and $R^8$ together with the N form a $C_2$-$C_6$ heterocyclic ring;

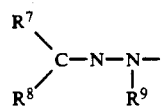
2)

wherein
$R^7$, $R^8$ and $R^9$ are independently hydrogen or $C_1$-$C_6$ alkyl, or $R^7$ and $R^8$ together with the carbon atom form a $C_3$-$C_7$ carbocyclic ring;
3) a) fully unsaturated, partially or fully reduced or substituted oxathiinyl; furanyl; dithiinyl; dioxinyl; thienyl; thiazolyl; oxazolyl; isoxazolyl; thiadiazolyl; pyrazolyl; pyrrolyl; pyranyl; oxathiazinyl; oxadiazolyl; or indolyl;
b) substituted or unsubstituted, linear or branched $C_1$-$C_8$ alkyl; $C_2$-$C_8$ alkenyl; $C_2$-$C_8$ alkynyl; $C_1$-$C_8$ mono- or di-alkylamino; $C_3$-$C_7$ cycloalkyl; $C_3$-$C_7$ cycloalkyl $C_1$-$C_6$ alkyl; $C_3$-$C_7$ cycloalkenyl unsubstituted or substituted by $C_1$-$C_6$ alkyl; or $C_7$-$C_8$ phenylalkyl; or
c) aryl, $C_7$-$C_{10}$ aralkyl or aryloxyalkyl or $C_3$-$C_8$ cycloalkylaryloxy wherein the aryl moiety of this group is naphthyl, phenyl or phenyl substituted by one or more halo, $C_1$-$C_8$ alkyl, carboxyl, $C_1$-$C_8$ haloalkyl, $C_1$-$C_8$ alkylthio, phenyl, nitro, amino, $C_1$-$C_8$ alkylcarbonylamino, hydroxyl, acetyl, acetyloxy, phenoxy; $C_1$-$C_8$ alkoxycarbonyl or $C_1$-$C_8$ alkylcarbonyl;
4) $R^{10}$—W— wherein
W is O, NH or $NR^f$ wherein $R^f$ is $C_1$-$C_4$ alkyl; and
$R^{10}$ is
i) a linear or branched, unsubstituted or halo-substituted $C_1$-$C_8$ alkyl, $C_2$-$C_8$ alkenyl, $C_2$-$C_8$ alkynyl; a $C_3$-$C_7$ cycloalkyl, $C_3$-$C_7$ cycloalkyl $C_1$-$C_6$ alkyl, $C_3$-$C_7$ cycloalkenyl unsubstituted or substituted by $C_1$-$C_6$ alkyl; an unsubstituted phenyl or phenyl substituted by halo, $C_1$-$C_6$ alkyl, $C_1$-$C_6$ alkoxy, carboxyl, $C_1$-$C_8$ haloalkyl, $C_3$-$C_7$ cycloalkyl, $C_1$-$C_8$ alkylthio, phenyl, nitro, amino, hydroxyl, acetyl acetyloxy, phenoxy, $C_1$-$C_8$ alkoxycarbonyl, $C_1$-$C_8$ alkylcarbonyl; furanylalkyl, tetrahydrofuranylalkyl, oxetanylalkyl, or oxiranylalkyl;
ii) $R^{11}$—$W^1$—$R^e$ wherein
$R^e$ is a linear or branched $C_1$-$C_6$ alkylidene;
$W^1$ is O or S; and
$R^{11}$ is linear or branched $C_1$-$C_4$ alkyl;
iii) $R^{13}R^{12}$—N—$R^e$ wherein
$R^e$ is as defined above; and
$R^{12}$ and $R^{13}$ are independently linear or branched $C_1$-$C_4$ alkyl;

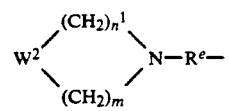
iv)

wherein
$R^e$ is as defined above;
$W^2$ is O, S, NH, $NR^{14}$ or $CR^{15}R^{16}$; wherein
$R^{14}$ is linear or branched $C_1$-$C_4$ alkyl;
$R^{15}$ and $R^{16}$ are independently, hydrogen, linear or branched $C_1$-$C_4$ alkyl; and
$n^1$ and m are independently 1, 2 or 3;
v) $R^{17}O_2C$—$R^e$ wherein
$R^e$ is as defined above; and
$R^{17}$ is linear or branched $C_1$-$C_6$ alkyl, $C_2$-$C_6$ alkenyl, $C_2$-$C_6$ alkynyl or $C_3$-$C_7$ cycloalkyl; $C_3$-$C_7$ cycloalkyl $C_1$-$C_6$ alkyl; $C_3$-$C_7$ cycloalkenyl unsubstituted or substituted by $C_1$-$C_6$ alkyl;
vi) U—$R^e$— wherein
$R^e$ is as defined above;
U is hydroxyl, acyloxy, aroyloxy, arylsulphonyloxy, $NO_2$, CN or $Si(CH_3)_3$;
vii) 1-adamantyl, 2-adamantyl or bornyl moieties;
viii) $Ar^1$—$R^e$— wherein
$R^e$ is as defined above; and
$Ar^1$ is phenyl or phenyl substituted independently with one to three halogen, mono-, di- or tri-halomethyl, nitro, $C_1$-$C_4$ alkyl, $C_2$-$C_4$ alkenyl, $C_1$-$C_4$ alkyloxy, $C_2$-$C_4$ alkenyloxy, or $C_2$-$C_4$ alkynyloxy; or
5) a $C_3$-$C_6$ sugar derivative.

Preferred among the compounds useful in the treatment of this invention are compounds of the formula:

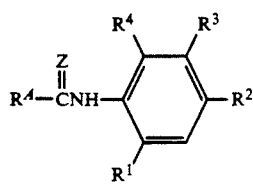

(II)

wherein
Z is O or S;
$R^4$ is
a) a fully unsaturated, partially or fully reduced or substituted oxathiinyl; a furanyl; a dithiinyl; a dioxinyl; a thienyl; a thiazolyl; an oxazolyl; an isoxazolyl; a thiadiazolyl; a pyrazolyl; a pyrrolyl; a pyranyl; an oxathiazinyl; or an oxadiazolyl;

(b) linear or branched $C_1$-$C_8$ alkyl; a $C_2$-$C_8$ alkenyl; a $C_2$-$C_8$ alkynyl; a $C_1$-$C_8$ alkoxy; a $C_2$-$C_8$ alkenyloxy; a $C_2$-$C_8$ alkynyloxy; a $C_3$-$C_8$ cycloalkyloxy; a $C_3$-$C_8$ cycloalkyl-alkoxy; a $C_1$-$C_8$ alkylamino; a $C_3$-$C_6$ cycloalkyl; a $C_3$-$C_6$ cycloalkenyl; a $C_7$-$C_8$ phenylalkyl; a $C_7$-$C_8$ phenoxyalkyl or a phenoxy; or (c) phenyl or phenyl substituted by one or more halo, a $C_1$-$C_8$ alkyl, a $C_1$-$C_8$ alkoxy, a carboxyl, a $C_1$-$C_8$ haloalkyl, a $C_1$-$C_8$ alkylthio, a phenyl, an amino, an acetamido, a hydroxyl, an acetyl, an acetyloxy, a phenoxy; a $C_1$-$C_8$ alkoxycarbonyl or a $C_1$-$C_8$ alkylcarbonyl;

$R^1$, $R^2$, $R^3$ and $R^4$ are as defined in formula I.

More preferred among the compounds useful in the treatment of this invention are compounds of the formula II wherein
Z is O or S;
$R^4$ is
(a) a dihydro-3-oxathiinyl; a furanyl; a dihydrofuranyl, a thienyl, a dihydro-2-dithiinyl; or a dihydro-2-dioxinyl; which can be substituted by one to three alkyl or alkoxyalkyl groups wherein the alkyl group is $C_1$-$C_4$;

(b) a phenyl; or a phenyl substituted by a group selected from a $C_1$-$C_8$ alkyl; a halogen; a $C_1$-$C_8$ haloalkyl; a $C_1$-$C_8$ alkylthio; a $C_1$-$C_8$ alkylthio; a carboxyl; an amino; an acetamido; a $C_1$-$C_8$ alkoxy; $C_1$-$C_8$ alkoxycarbonyl; a hydroxyl; a $C_1$-$C_8$ alkylcarboxyl; a phenyl or a phenoxy group;

(c) a linear or branched $C_1$-$C_8$ alkyl; a $C_2$-$C_8$ alkenyl; a $C_2$-$C_8$ alkynyl; a $C_1$-$C_8$ alkoxy; a $C_2$-$C_8$ alkenyloxy; a $C_2$-$C_8$ alkynyloxy; a $C_3$-$C_8$ cycloalkyloxy; a $C_3$-$C_8$ cycloalkylalkoxy; a $C_1$-$C_8$ alkyl amino; $C_3$-$C_7$ cycloalkyl; $C_3$-$C_7$ cycloalkyl $C_1$-$C_6$ alkyl; $C_3$-$C_7$ cycloalkenyl unsubstituted or substituted by $C_1$-$C_6$ alkyl or a phenoxy group; and wherein $R^1$, $R^2$, $R^3$, and $R^4$, have the meanings given above in formula I.

In particular, the preferred group of oxathiin derivatives comprise those of formula III:

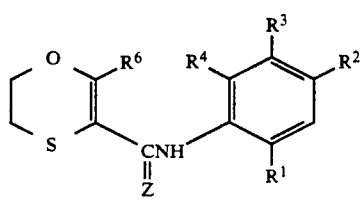

(III)

wherein
Z is O or S;
$R^6$ is an alkyl or alkoxyalkyl wherein the alkyl groups are independently $C_1$-$C_4$; and
$R^1$, $R^2$, $R^3$ and $R^4$ have the meanings given above in formula I.

A particularly preferred group of compounds has the formula IV

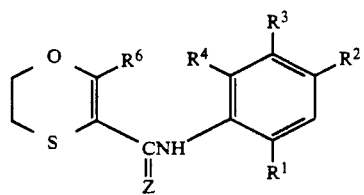

(IV)

wherein
Z is O or S;
$R^1$ is a hydrogen, a fluoro or a methyl group;
$R^2$ is a hydrogen, a chloro, a fluoro or a methyl group;
$R^3$ is $COOR^5$ wherein $R^5$ is an alkyl group of 1 to 6 carbon atoms;
$R^4$ is hydrogen; and
$R^6$ is a methyl, ethyl or propyl group.

Furan derivatives found useful in the method of the invention comprise compounds of formula V a and V b:

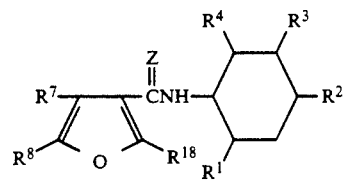

(Va)

or

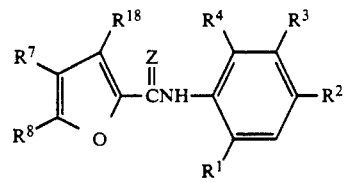

(Vb)

wherein Z is O or S; $R^7$ and $R^8$ are independently hydrogen or a methyl; $R^{18}$ is hydrogen, methyl or ethyl; and $R^1$, $R^2$, $R^3$, and $R^4$ have the meanings given above in formula I.

Preferred compounds of this group comprise those of the above formulas Va and Vb wherein $R^1$ and $R^4$ are hydrogen; $R^2$ is a halogen; and $R^3$ is $COOR^5$ wherein $R^5$ is an alkyl group of 1 to 6 carbon atoms.

Another group of effective compounds has the formula VI:

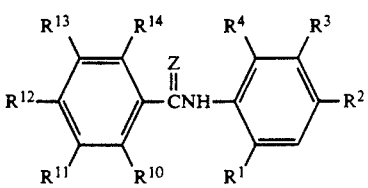

(VI)

wherein Z, $R^1$, $R^2$, $R^3$ and $R^4$ have the meanings given above in formula I and $R^{10}$, $R^{11}$, $R^{12}$, and $R^{13}$ are independently hydrogen or halogen; and $R^{14}$ is hydrogen; a halogen; a $C_1$–$C_4$ alkyl; a $C_1$–$C_4$ alkoxy; a $C_1$–$C_4$ haloalkyl; a $C_1$–$C_4$ alkylthio; an amino; a $C_1$–$C_8$ alkylcarbonylamino; a hydroxyl; an acetyl; an acetyloxy; or acetylamino.

More preferred compounds of formula VI are those wherein $R^1$ is hydrogen or fluoro; $R^{10}$, $R^{11}$, $R^{12}$, and $R^{13}$ are hydrogen; $R^{14}$ is hydrogen, methyl, ethyl, a chloro, an iodo, an amino, a bromo, a fluoro, a methylthio, a methoxy, or a hydroxyl.

Dioxin derivatives that may be utilized in the method for inhibiting the growth or replication of HIV comprise compounds of formula VII:

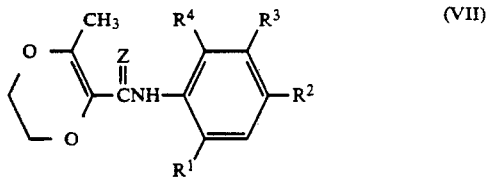

wherein Z, $R^1$, $R^2$, $R^3$ and $R^4$ have the meanings given above in formula I.

More preferred dioxin compounds are those wherein $R^1$ and $R^4$ are hydrogen; and $R^3$ is a $COOR^5$ group in which $R^5$ has the meaning given above in formula I.

Preferred derivatives of acyclic carboxamides or carbamates useful in the method hereof comprise compounds of formula VIII:

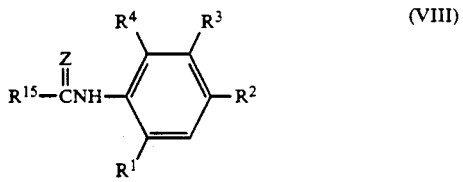

wherein $R^{15}$ is a linear or branched $C_3$–$C_6$ alkyl; a $C_2$–$C_6$ alkenyl or alkynyl; a $C_7$–$C_8$ aralkyl or aryloxyalkyl; a $C_1$–$C_8$ alkoxy; a $C_2$–$C_8$ alkenyloxy or alkynyloxy; a $C_1$–$C_8$ aryloxy; $C_3$–$C_7$ cycloalkyl; $C_3$–$C_7$ cycloalkyl $C_1$–$C_6$ alkyl; $C_3$–$C_7$ cycloalkenyl unsubstituted or substituted by $C_1$–$C_6$ alkyl; a $C_3$–$C_8$ cycloalkyloxy, cycloalkylalkyloxy, cycloalkylaryloxy or alkylamino; and Z, $R^1$, $R^2$, $R^3$ and $R^4$ have the meanings given above in formula I.

More preferred compounds are those wherein $R^1$ is a hydrogen or a fluoro; $R^2$ has the meaning given above in formula I; $R^3$ is a $COOR^5$ wherein $R^5$ has the meaning given above in formula I; $R^4$ is a hydrogen and $R^{15}$ can be a $C_3$–$C_6$ alkyl; a $C_2$–$C_6$ alkenyl or alkynyl; a $C_7$–$C_8$ phenylalkyl or phenoxyalkyl; a $C_1$–$C_8$ alkoxy; a $C_2$–$C_8$ alkenyloxy or alkynyloxy; phenoxy; $C_3$–$C_7$ cycloalkyl; $C_3$–$C_7$ cycloalkyl $C_1$–$C_6$ alkyl; $C_3$–$C_7$ cycloalkenyl unsubstituted or substituted by $C_1$–$C_6$ alkyl; $C_3$–$C_8$ cycloalkoxy or cycloalkylalkyloxy; cycloalkyl- phenyloxy or alkylamino.

Effective compounds are those compounds of formula VIII wherein $R^{15}$ is a $C_3$–$C_6$ cycloalkyl or cycloalkenyl group and $R^1$–$R^4$ have the meanings of formula I.

A subgroup of compounds of formula VIII are those wherein $R^1$ and $R^4$ are hydrogen and $R^3$ is a $COOR^5$ group wherein $R^5$ has the meaning given above.

Dithiin derivatives found most useful in the method hereof comprise compounds of formula IX:

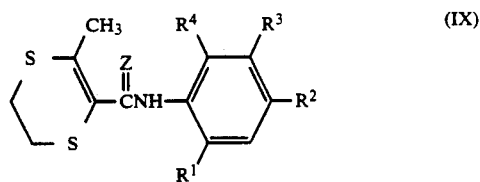

wherein Z and $R^1$–$R^4$ have the meanings given above in formula I.

The preferred compounds of formula IX are those wherein $R^1$ and $R^4$ are hydrogen; $R^2$ is a hydrogen or a chloro; and $R^3$ is a $C_2$–$C_6$ alkoxycarbonyl group.

Various carbonylamino derivatives of oxathiins are known. Thus, the preparation and use of various 5,6-dihydro-2-methyl-1,4-oxathiin-3-carboxamides (which may also be termed 2,3-dihydro-5-carboxamido-6-methyl-1,4-oxathiins) as bactericides, fungicides and plant viricides, particularly for agricultural purposes, is disclosed in U.S. Pat. Nos. 3,249,499; 3,402,241; 3,454,391; 3,657,449; 3,806,332; 4,182,716; 4,247,707; and 4,359,579.

One such compound, carboxin, viz. 5,6-dihydro-2-methyl-N-phenyl-1,4-oxathiin-3-carboxamide (previously termed 5,6-dihydro-2-methyl-1,4-oxathiin-3-carboxanilide), is commercially marketed as a systemic plant fungicide providing control by seed treatment of various fungi that cause seed and seedling diseases in a variety of crops.

Certain of the particular oxathiin derivatives useful in the present method are also disclosed in White et al., Pesticide Biochemistry and Physiology, 9, 165 (1978). In particular, White et al. discloses that methyl 3-[[(5,6-dihydro-2-methyl-1,4-oxathiin-3-yl) carbonyl]amino]-benzoate and ethyl 3-[[(5,6-dihydro-2-methyl-1,4-oxathiin-3-yl)carbonyl]amino]benzoate (Example 8 below) are inhibitors of succinate dehydrogenase complex in mitochondria from Ustilago maydis, the corn smut fungus.

This publication neither discloses nor suggests that either of the noted compounds is useful in inhibiting the growth or replication of viruses of the HIV class.

In accordance with a further aspect of the present invention, there is provided a class of novel compounds useful in inhibiting the growth or replication of HIV, which compounds have not previously been described in the literature. The subset of novel compounds which may be so utilized comprises the furanyl-, phenyl-, dithiinyl-, dioxinyl-, alkoxy-, and alkyl-carbonylamino derivatives of Formula (I) above, and the oxathiinyl- derivative of Formula (II) other than those in which the carboalkoxy moiety on the aryl nucleus is carbomethoxy or carboethoxy and $R_1$, $R_2$ and $R_4$ are all hydrogen.

The compounds useful in accordance with the present invention may be prepared by the methods described in von Schmeling et al, see U.S. Pat. No. 3,249,499, at col. 2, line 34 to col. 3 line 73; or Znotins et al, see U.S. Pat. No. 4,182,716, at col. 2, line 3 to col. 2, line 68.

When $R^4$ is a $C_3$ to $C_6$ sugar derivative, it is one of the following:

A) A $C_3$ sugar derivative of the general structure $CH_2OeP^ICHOP^{II}—CH_2—$, where $P^I$ and $P^{II}$ are both H or a combination of H and a suitable protecting group (i.e. a mono-protected sugar) or two such protecting groups. Suitable protecting groups are an alkyl or aryl ether, an alkyl or aryl ester, an alkyl or aryl silyl ether or a cyclic protecting group (i.e. $P^I$ and $P^{II}$ are connected to each other) such as acetal, a ketal, an ortho ester or a cyclic ester. The sugar is of either the D configuration, the L configuration or a racemic mixture of both configurations.

B) A $C_4$ sugar derivative of the general structure $CH_2OP^I—CHOP^{II}—CHOP^{III}—CH_2$ where $P^I$, $P^{II}$ and $P^{III}$ are defined as above. Also considered are the five-membered (furanose) cyclic forms of the parent aldoses, as indicated in the figure below. These sugars are of the stereochemical configurations corresponding to the structures designated by the names erythritol (erythrose) or threitol (threose), in either their D, L or racemic forms. In the case of the cyclic forms, both the $\alpha$ and $\beta$ anomers are included.

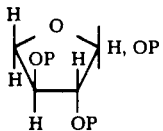

C) A $C_5$ sugar aldose or ketose derivative in either one of the following forms: i) a suitably protected linear form of the corresponding sugar alcohols, analogous to that described in (B); ii) their five-membered (furanose) or six-membered (pyranose; see below for an example) cyclic forms, which are attached to Y through either a primary or secondary carbon and where protecting groups are as described above. These sugars are the D, L or racemic forms (plus the $\alpha$ and $\beta$ anomers, if applicable) of the structures corresponding to the configurations described by the common names ribose, arabinose, xylose and lyxose (aldoses) or xylulose and ribulose (ketoses). Also considered are the distinct desoxy forms of these sugars where one of the O-protecting groups is missing and is replaced by H or $CH_3$.

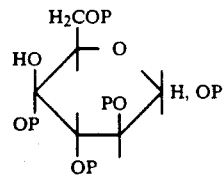

D) A $C_6$ sugar aldose or ketose in either one of the following forms: i) a suitably protected linear form of the corresponding sugar alcohols, analogous to that described in (C); ii) five-membered (furanose) or six-membered (pyranose) cyclic forms. The sugar is attached to Y through either a primary or secondary carbon and the protecting groups are those described above. The sugars are the D, L, or racemic forms (plus the $\alpha$ and $\beta$ anomers, where applicable) of the structures corresponding to the stereochemical configurations described by the common names allose, altrose, glucose, gulose, mannose, idose, galactose, talose (aldohexoses) and fructose, sorbose, psicose and tagatose (2-ketohexoses). Also considered are the known desoxy forms of the aforementioned sugars as described in (C) that are distinct from previously mentioned compounds.

GENERAL SYNTHETIC METHODS FOR PREPARING EACH CLASS OF COMPOUNDS

Compounds of formula II, wherein Z is O and $R^4$ is oxathiinyl, furanyl, dithiinyl, dioxinyl, other heterocyclyl, substituted phenyl or alkyl, may be prepared from the appropriate carboxylic acid, $R^4COOH$, and an aniline derivative, i.e.,

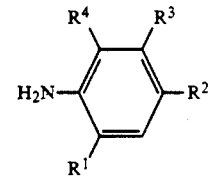

by employing one of the conventional methods of amide bond formation. For example, the carboxylic acid may be converted to an acid halide, such as the acid chloride, $R^4COCl$, which may then be reacted with the aniline derivative to form the amide (I). The amide-forming reaction is carried out in an appropriate solvent, such as methylene chloride, toluene, methyl ethyl ketone, tetrahydrofuran, dimethylformamide or acetonitrile, at a temperature of about 0° C. to about 100° C. It is usually preferable to carry out the reaction in the presence of a base, such as triethylamine or pyridine. Other reactive derivatives of the carboxylic acid may be employed: for example the anhydride of the carboxylic acid or a mixed anhydride, such as an alkoxycarbonyloxy derivative, may be reacted with the aniline derivative. Alternatively, the carboxylic acid and aniline derivative may be reacted directly in the presence of a condensing agent, such as dicyclohexylcarbodiimide, to form the amide.

The aniline derivatives may be prepared by reduction of the corresponding nitro compounds by well-known methods, for example with hydrogen and a catalyst, such as Raney nickel or platinum, or with a metal-acid combination, such as iron or tin and hydrochloric or acetic acid. Where $R^3$ is $COOR^5$, the $R^5$ group may be introduced by esterification of the corresponding aminobenzoic acid or nitrobenzoic acid by conventional methods.

Other compounds of formula II wherein $R^4$ is an alkoxy may be prepared by reacting the appropriate aniline derivative with an alkoxycarbonyl chloride under conditions essentially similar to those used for reaction of an acid chloride with the aniline derivative. They may also be prepared by reacting the appropriate isocyanate derivative with an alcohol. The isocyanate may be prepared by reacting the aniline derivative or a suitable salt thereof, such as the hydrochloride, with phosgene or a phosgene substitute, such as trichloromethyl chloroformate.

Compounds of formula II, wherein $R^3$ is $COOR^5$ or $COSR^5$, may also be prepared from the appropriate carbonylaminobenzoic acid i.e.,

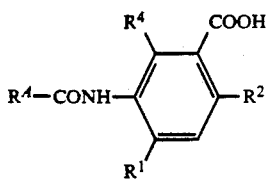

or a corresponding derivative thereof, such as the acid chloride, by using a conventional esterification method. For example, the acid may be reacted with the alcohol, $R^{50}H$, or thiol, $R^5SH$, in the presence of one of the common esterification catalysts, such as hydrogen chloride, sulfuric acid, methanesulfonic acid, p-toluenesulfonic acid, thionyl chloride or phosphorus pentachloride. The alcohol itself may serve as the solvent, or the esterification can be carried out in a compatible solvent such as toluene, methylene chloride or tetrahydrofuran. Esterification may also be accomplished by reacting the acid chloride with the above alcohol or thiol, in which case the presence of a base, such as triethylamine or pyridine, may be advantageous. Esters may also be obtained by reacting an alkali metal salt of the acid with the halide, $R^5Hal$.

The carbonylaminobenzoic acid derivatives may be prepared by reacting the corresponding aminobenzoic acid with an acid chloride, $R^4COCl$, or by hydrolyzing a compound of formula II, wherein $R^3$ is $COOR^5$ and $R^5$ is preferably a lower alkyl group (such as methyl or ethyl), for example by reaction with sodium or potassium hydroxide followed by acidification.

Oxathiin derivatives of formula II may be prepared by reacting a 5,6-dihydro-1,4-oxathiin-3-carbonyl chloride derivative with an aniline compound in a suitable solvent, such as methylene chloride or toluene, in the presence of a base, such as triethylamine or pyridine:

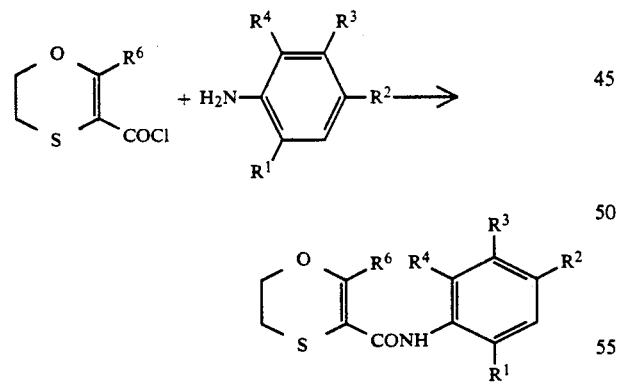

The acid chloride may be made by conventional methods from the 5,6-dihydro-1,4-oxathiin-3-carboxylic acid, which is made in turn from the appropriate mercaptoethanol derivative and methyl or ethyl 2-chloro-3-oxoalkanoate by the method described in U.S. Pat. No. 3,249,499 (col 3, lines 46–66) for the preparation of 5,6-dihydro-2-methyl-1,4-oxathiin-3-carboxylic ɔ acid (named 2,3-dihydro-6-methyl-1,4-oxathiin-5-carboxylic acid or 2,3-dihydro-5-carboxy-6-methyl-1,4-oxathiin in the reference), as illustrated below:

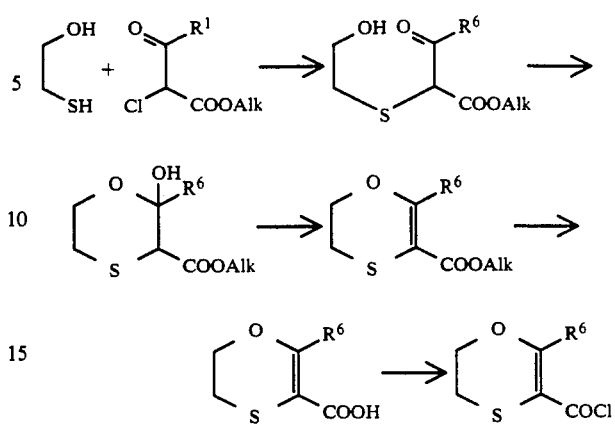

Certain compounds of formula II may also be prepared by reacting the aniline derivative with diketene to form the 1,3-dioxobutylamino derivative. This may be converted to the oxathiin by chlorination and reaction with mercaptoethanol by the method described in U.S. Pat. No. 3,249,499 (col 1, line 54 to col 2, line 67), as illustrated below:

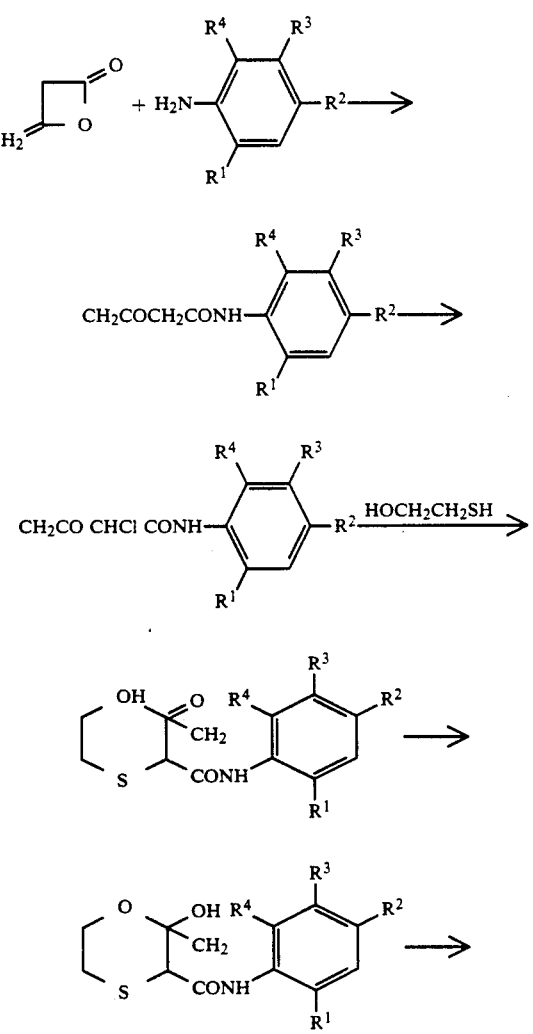

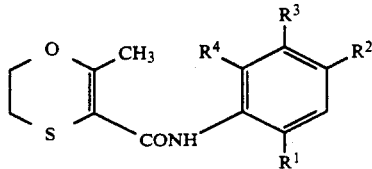

Alternatively, the 1,3-dioxobutylamino derivative may be converted to the oxathiin by the method described in U.S. Pat. No. 4,182,716 (col 2, line 3 to col 2, line 68) as illustrated below:

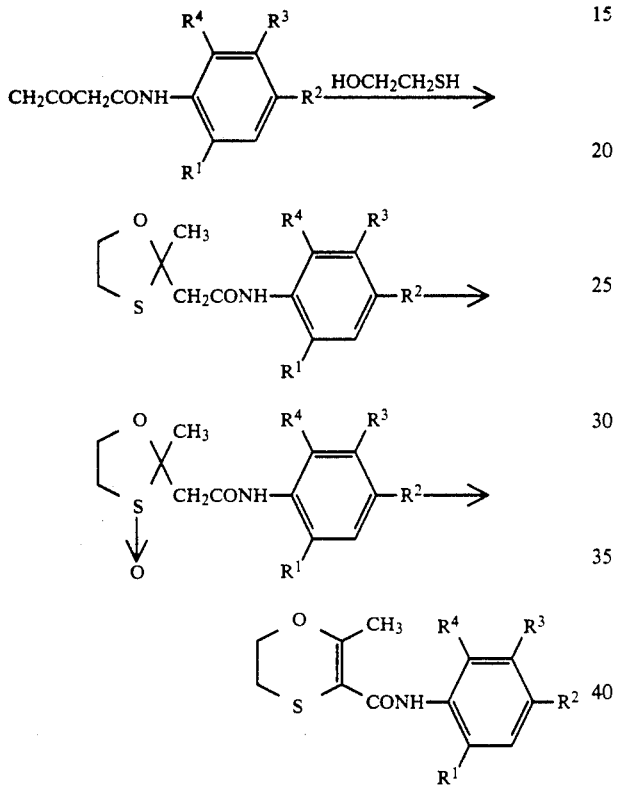

Oxathiins of formula II, wherein $R^3$ is $COOR^5$ or $COSR^5$, may also be prepared from the appropriate oxathiincarbonylaminobenzoic acid compound, i.e.,

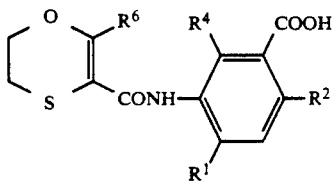

or a reactive derivative thereof, such as the acid chloride, by using a conventional esterification method. For example, the acid may be reacted with the alcohol, $R^5OH$, or thiol, $R^5SH$, in the presence of one of the common esterification catalysts, or by reacting the acid chloride with the alcohol or thiol, if necessary, in the presence of a base such as triethylamine or pyridine. Esterification may also be accomplished by reacting an alkali metal salt of the acid with the halide, $R^5Hal$.

The oxathiincarbonylaminobenzoic acid derivatives may be prepared by reacting the appropriate 5,6-dihydro-1,4-oxathiin-3-carbonyl chloride and aminobenzoic acid derivatives, or by hydrolyzing an oxathiin of formula II, wherein $R^3$ is $OR^5$ and $R^5$ is preferably a lower alkyl group (such as methyl or ethyl), for example by reaction with sodium or potassium hydroxide followed by acidification.

Thiocarbamates, thioureas and thiocarboxanilides are important and active compounds of the invention. Thiocarbamates and thioureas are made by taking alcohols and amines and reacting them with the appropriate isothiocyanate. Thus to make compounds of the formula II type:

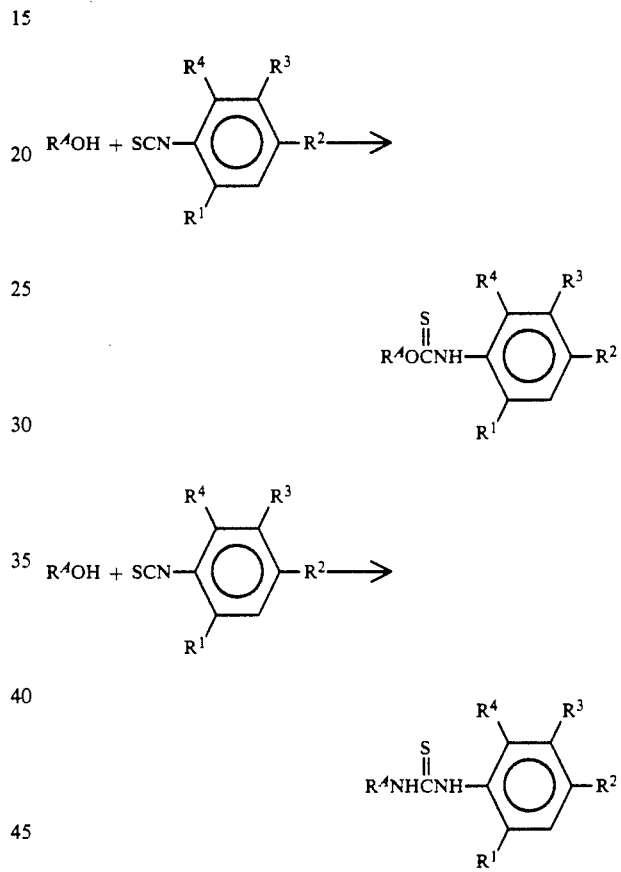

The isothiocyanate is made using the appropriate aniline derivative or suitable salt thereof, such as the hydrochloride, with thiophosgene.

Alternatively, esters of these thiocarbamates can be made using a carboxylic acid and appropriate alcohol in the presence of dicyclohexylcarbodiimide (DCC) and a base catalyst such as 4-dimethylaminopyridine (DMAP). A preferred carboxylic acid is 2-chloro-5-[[(1-methylethoxy)thioxomethyl]amino]benzoic acid.

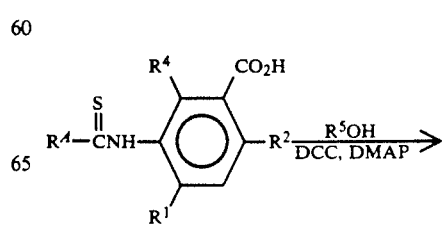

-continued

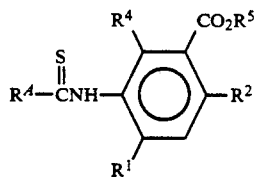

Thiocarboxanilides can be prepared starting from the corresponding amide and reacting it with a sulfurating agent such as Lawesson's reagent or phosphorus pentasulphide.

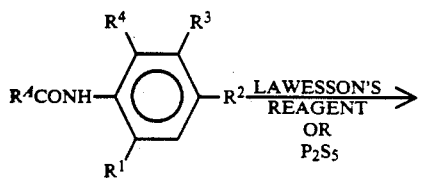

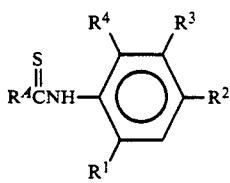

The compounds of this invention, as noted hereinabove, are useful for inhibiting the growth or replication of viruses of the HIV group, at present known to include HIV-I and HIV-II. The present compounds also may be used in those individuals who have been exposed to HIV but have not been infected, as a prophylactic measure to prevent infection by HIV. They may be used alone or in combination with other chemotherapeutic agents either prophylactically or to combat an active infection.

The dosage levels at which the compounds of the invention are employed in human therapy may, of course, be adjusted to provide optimum therapeutic response. For example, several divided doses may be administered daily or the dose may be proportionally reduced, as indicated by the exigencies of the therapeutic situation.

It may be advantageous to formulate the compositions in unit dosage forms for ease of administration and uniformity of dosage. "Unit dosage form," as that term is used herein, refers to a physically discrete unit suitable for use as a unitary dosage for mammalian subjects to be treated. Each unit contains a predetermined quantity of active material calculated to produce the desired therapeutic effect, in association with the required pharmaceutically acceptable carrier. Specifications for unit dosage forms are dictated by and directly depend on (a) the unique characteristics of the active material and the particular therapeutic effect to be achieved and (b) the limitations inherent in the art of compounding such an active material for the treatment of HIV infections in living subjects without excessive cytotoxic side effects.

The active compounds may suitably be administered parenterally, intraperitoneally, intrathecally, intravenously, orally, or as an aerosol. Solutions or dispersions of the active compounds can be prepared, e.g., in glycerol, liquid polyethylene glycols, and mixtures thereof, and in oils. For ordinary conditions of storage and use, these preparations usually contain a preservative to prevent the growth of microorganisms.

The pharmaceutical forms suitable for injectable use include sterile aqueous solutions or dispersions and sterile powders for the extemporaneous preparation of sterile injectable solutions or dispersions. For such uses the form must be sterile and must be fluid to the extent necessary to provide easy syringeability. It must be stable under the conditions of manufacture and storage and must be preserved against the contaminating action of microorganisms such as bacteria and fungi.

The carrier can be a solvent or dispersing medium containing, for example, water, ethanol, a polyol (glycerol, propylene glycol, liquid polyethylene glycol, and the like), suitable mixtures thereof, and vegetable oils. The proper fluidity can be maintained, for example, by the use of a coating such as lecithin, by the maintenance of the required particle size in the case of a dispersion, and by the use of surfactants. Prevention of the action of microorganisms can be insured by various anti-bacterial and antifungal agents, for example, paraben, chlorobutanol, phenol, sorbic acid, and thimerosal. Other agents may be used. In many cases it may be preferable to include isotonic agents, for example, sugars or sodium chloride, in the dosage form. Prolonged absorption of the injectable formulations can be effected by incorporating therein agents delaying absorption, for example, aluminum monostearate and gelatin.

Sterile injectable solutions are prepared by incorporating the active compound in the appropriate solvent, in admixture with various of the other ingredients enumerated above, as required, followed by filtered sterilization. Generally, dispersions are prepare by incorporating the sterilized active ingredient in a sterile vehicle that contains the dispersing medium and any other required ingredients. When, on the other hand, sterile powders are used to prepare sterile injectable solutions, it is preferred to subject a sterile, filtered solution of the desired ingredients to vacuum drying or freeze-drying, yielding a powder of the active ingredient plus any additional desired ingredients.

As used herein, a "pharmaceutically acceptable" carrier or excipient includes solvents, dispersing media, coatings, antibacterial and antifungal agents, isotonic and absorption delaying agents and the like. The use of such media and agents as carriers or excipients for pharmaceutically active substances is well known in the art. Except insofar as any conventional medium or agent is incompatible with the active ingredients of the present invention or toxic, its use in the therapeutic formulations of the invention is contemplated. Supplementary active ingredients can also be incorporated in the present formulation.

The invention will be further described with reference to the following Examples, but the invention is not meant to be limited to the details described therein.

In the Examples, percent (%) is by weight. Nuclear magnetic resonance data is shown as NMR.

Table I and Tables IA through IE below summarize the structures of the compounds of the Examples having reference to the preceding general formulas.

TABLE I

| Compounds Prepared |
| --- |
| Oxathiins |

TABLE I-continued

Compounds Prepared

| Compound | $R^1$ | $R^2$ | $R^3$ | $R^4$ | $R^6$ |
|---|---|---|---|---|---|
| 1 | H | Cl | CO2iPr | H | Me |
| 1-Methylethyl 2-chloro-5-[[(5,6-dihydro-2-methyl-1,4-oxathiin-3-yl)carbonyl]amino]benzoate | | | | | |
| 2 | F | Cl | CO2iPr | H | Me |
| 1-Methylethyl 2-chloro-5-[[(5,6-dihydro-2-methyl-1,4-oxathiin-3-yl)carbonyl]amino]-4-fluorobenzoate | | | | | |
| 3 | H | Cl | CO2Me | H | Me |
| Methyl 2-chloro-5-[[(5,6-dihydro-2-methyl-1,4-oxathiin-3-yl)carbonyl]amino]benzoate | | | | | |
| 4 | H | Cl | CO2Et | H | Me |
| Ethyl 2-chloro-5-[[(5,6-dihydro-2-methyl-1,4-oxathiin-3-yl)carbonyl]amino]benzoate | | | | | |
| 5 | H | Cl | CO2Pr | H | Me |
| Propyl 2-chloro-5-[[(5,6-dihydro-2-methyl-1,4-oxathiin-3-yl)carbonyl]amino]benzoate | | | | | |
| 6 | H | Cl | CO2Bu | H | Me |
| Butyl 2-chloro-5-[[(5,6-dihydro-2-methyl-1,4-oxathiin-3-yl)carbonyl]amino]benzoate | | | | | |
| 7 | H | Cl | CO2iPr | H | Et |
| 1-Methylethyl 2-chloro-5-[[(2-ethyl-5,6-dihydro-1,4-oxathiin-3-yl)carbonyl]amino]benzoate | | | | | |
| 8 | H | H | CO2Et | H | Me |
| Ethyl 3-[[(5,6-dihydro-2-methyl-1,4-oxathiin-3-yl)carbonyl]amino]benzoate | | | | | |
| 9 | H | H | CN | H | Me |
| N-(3-Cyanophenyl)-5,6-dihydro-2-methyl-1,4-oxathiin-3-carboxamide | | | | | |
| 10 | H | H | CO2iPr | H | Me |
| 1-Methylethyl 3-[[(5,6-dihydro-2-methyl-1,4-oxathiin-3-yl)carbonyl]amino]benzoate | | | | | |
| 11 | H | Cl | CO2Et | H | Et |
| Ethyl 2-chloro-5-[[(2-ethyl-5,6-dihydro-1,4-oxathiin-3-yl)carbonyl]amino]benzoate | | | | | |
| 12 | F | Me | CO2iPr | H | Me |
| 1-Methylethyl 5-[[(5,6-dihydro-2-methyl-1,4-oxathiin-3-yl)carbonyl]amino]-4-fluoro-2-methylbenzoate | | | | | |
| 13 | F | H | CO2iPr | H | Me |
| 1-Methylethyl 3-[[(5,6-dihydro-2-methyl-1,4-oxathiin-3-yl)carbonyl]amino]-4-fluorobenzoate | | | | | |
| 14 | Me | H | CO2Et | H | Me |
| Ethyl 3-[[(5,6-dihydro-2-methyl-1,4-oxathiin-3-yl)carbonyl]amino]-4-methylbenzoate | | | | | |
| 15 | H | Cl | CO2n-Pentyl | H | Me |
| Pentyl 2-chloro-5-[[(5,6-dihydro-2-methyl-1,4-oxathiin-3-yl)carbonyl]amino]benzoate | | | | | |
| 69 | H | Cl | CO2(CH2)2—OCH3 | H | CH3 |
| 2-Methoxyethyl 2-chloro-5-[[5,6-dihydro-2-methyl-1,4-oxthiin-3-yl)carbonyl]amino]benzoate M.P. °C.: syrup | | | | | |
| 70 | H | Cl | CO2Et | H | nPr |
| Ethyl 2-chloro-5-[[(5,6-dihydro-2-propyl-1,4-oxathiin-3-yl)carbonyl]amino]benzoate M.P. °C.: 66–66.5 | | | | | |
| 71 | H | Cl | CO2CH3 | H | nPr |
| Methyl 2-chloro-5-[[(5,6-dihydro-2-propyl-1,4-oxathiin-3-yl)-carbonyl]amino]benzoate M.P. °C.: 77–78 | | | | | |
| 72 | H | F | CO2iPr | H | Me |
| 1-Methylethyl 5-[[5,6-dihydro-2-methyl-1,4-oxathiin-3-yl)carbonyl]amino]-2-fluorobenzoate M.P. °C.: 123–125 | | | | | |
| 73 | H | Me | CO2iPr | H | Me |
| 1-Methylethyl 5-[[5,6-dihydro-2-methyl-1,4-oxathiin-3-yl)carbonyl]amino]-2-methylbenzoate M.P. °C.: 95–97 | | | | | |
| 74 | H | Cl | CO2CH2iPr | H | Et |
| 2-Methylpropyl 2-chloro-5-[[(2-ethyl-5,6-dihydro-1,4-oxathiin-3-yl)carbonyl]amino]benzoate M.P. °C.: 78–80 | | | | | |
| 75 | Me | H | CO2nPr | H | Me |

TABLE I-continued

Compounds Prepared

Propyl 3-[[(5,6-dihydro-2-methyl-1,4-oxathiin-3-yl)carbonyl]amino]-4-methylbenzoate
M.P. °C.: 87-88

| | | | | | |
|---|---|---|---|---|---|
| 76 | H | H | CO$_2$nBu | H | Me |

Butyl 3-[[5,6-dihydro-2-methyl-1,4-oxathiin-3-yl)carbonyl]amino]benzoate
M.P. °C.: 112-113

| | | | | | |
|---|---|---|---|---|---|
| 77 | F | F | CO$_2$iPr | H | Me |

1-Methylethyl 5[[(5,6-dihydro-2-methyl-1,4-oxathiin-3-yl)carbonyl]amino]-2,4-difluorobenzoate
M.P. °C.: 132-133

| | | | | | |
|---|---|---|---|---|---|
| 78 | H | Cl | CO$_2$(CH$_2$)$_2$O—(CH$_2$)$_2$OCH$_3$ | H | Me |

2-(2-Methoxyethoxy)ethyl 2-chloro-5-[[(5,6-dihydro-2-methyl-1,4-oxathiin-3-yl)carbonyl]amino]benzoate
M.P. °C.: syrup

| | | | | | |
|---|---|---|---|---|---|
| 110 | H | Cl | CO$_2$C$_6$H$_{11}$(CYCLO) | H | CH$_3$ |

Cyclohexyl 2-chloro-5-[[5,6-dihydro-2-methyl-1,4-oxathiin-3-yl)carbonyl]amino]benzoate
Oil

| | | | | | |
|---|---|---|---|---|---|
| 111 | H | Cl | CO$_2$C$_5$H$_9$(CYCLO) | H | CH$_3$ |

Cyclopentyl 2-chloro-5-[[(5,6-dihydro-2-methyl-1,4-oxathiin-3-yl)carbonyl]amino]benzoate
M.P. °C.: 112-113

| | | | | | |
|---|---|---|---|---|---|
| 112 | H | OH | CO$_2$iPr | H | CH$_3$ |

1-Methylethyl 5-[[(5,6-dihydro-2-methyl-1,4-oxathiin-3-yl)-carbonyl]amino]-2-hydroxybenzoate

| | | | | | |
|---|---|---|---|---|---|
| 147 | H | H | H | CONHR$^H$ | CH$_3$ |

M.P. °C.: 202-203

| | | | | | |
|---|---|---|---|---|---|
| 157 | H | OC(O)CH$_3$ | CO$_2$IPr | H | CH$_3$ |

M.P. °C.: 99-101

| | | | | | |
|---|---|---|---|---|---|
| 158 | H | OC(O)ET | CO$_2$IPr | H | CH$_3$ |

M.P. °C.: 135-137

Furans

Compound

16

[Structure: 2,4,5-trimethyl-3-furanyl group with CONH linker to phenyl ring bearing COOiPr and Cl substituents]

1-Methylethyl 2-chloro-5-[[(2,4,5-trimethyl-3-furanyl)carbonyl]amino]benzoate

17

[Structure: 3-methyl-2-furanyl group with CONH linker to phenyl ring bearing COOiPr and Cl substituents]

1-Methylethyl 2-chloro-5-[[(3-methyl-2-furanyl)carbonyl]amino]benzoate 79  1-Methylethyl 2-chloro-5-[[(2-methyl-3-furanyl)carbonyl]amino]benzoate
M.P. °C.: 90-91

80  1-Methylethyl 2-chloro-5-[[(2,4-dimethyl-3-furanyl)carbonyl]amino]benzoate
M.P. °C.: 126-127

81  1-Methylethyl 2-chloro-5-[[(2,5-dimethyl-3-furanyl)carbonyl]amino]benzoate
M.P. °C.: 132-134

113  1-Methylethyl 2-chloro-5-[(2-furanylcarbonyl)-amnio]benzoate
M.P. °C.: 141-142

Aromatics

[Structure: Two phenyl rings connected by CONH. Left ring has substituents $R^{10}$, $R^{11}$, $R^{12}$, $R^{13}$, $R^{14}$. Right ring has substituents $R^1$, $R^2$, $R^3$.]

| Compound | $R^1$ | $R^2$ | $R^3$ | $R^{10}$ | $R^{11}$ | $R^{12}$ | $R^{13}$ | $R^{14}$ |
|---|---|---|---|---|---|---|---|---|
| 18 | F | Cl | CO$_2$iPr | H | H | H | H | H |

1-Methylethyl 5-(benzoylamino)-2-chloro-4-fluorobenzoate

TABLE I-continued

Compounds Prepared

| # | | | | | | | | |
|---|---|---|---|---|---|---|---|---|
| 19 | H | Cl | CO$_2$iPr | H | H | H | H | OMe |

1-Methylethyl 2-chloro-5-[(2-methoxybenzoyl)amino]benzoate

| 20 | F | Cl | CO$_2$iPr | Br | Br | Br | Br | CO$_2$H |

2,3,4,5-Tetrabromo-6-[[[4-chloro-2-fluoro-5-[(1-methylethoxy)carbonyl]phenyl]amino]carbonyl]benzoic acid

| 21 | H | Cl | CO$_2$iPr | Br | Br | Br | Br | CO$_2$H |

2,3,4,5-Tetrabromo-6-[[[4-chloro-3-[(1-methylethoxy)carbonyl]phenyl]amino]carbonyl]benzoic acid

| 22 | H | Cl | CO$_2$iPr | Cl | Cl | Cl | Cl | CO$_2$H |

2,3,4,5-Tetrachloro-6-[[[4-chloro-3-[(1-methylethoxy)carbonyl]phenyl]amino]carbonyl]benzoic acid

| 23 | H | Cl | CO$_2$iPr | H | H | H | H | Me |

1-Methylethyl 2-chloro-5-[(2-methylbenzoyl)amino]benzoate

| 24 | H | Cl | CO$_2$nPr | H | H | H | H | Me |

Propyl 2-chloro-5-[(2-methylbenzoyl)amino]benzoate

| 25 | H | Cl | CO$_2$iPr | H | H | H | H | F |

1-Methylethyl 2-chloro-5-[(2-fluorobenzoyl)amino]benzoate
M.P. °C.: 53–56

| 82 | H | Cl | CO$_2$iPr | H | H | H | H | I |

1-Methylethyl 2-chloro-5-[(2-iodobenzoyl)amino]benzoate
M.P. °C.: 120–120.5

| 83 | H | Cl | 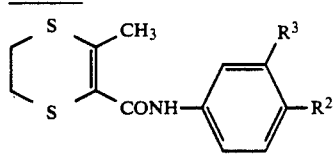 | H | H | H | H | OCH$_3$ |

Tetrahydro-2-furanylmethyl 2-chloro-5-[(2-methoxybenzoyl)-amino]benzoate
M.P. °C.: 75–77

| 84 | H | Cl | CO$_2$(CH$_2$)$_2$OCH$_3$ | H | H | H | H | H |

2-Methoxyethyl 5-[benzoylamino]-2-chlorobenzoate
M.P. °C.: syrup

| 85 | H | Cl | CO$_2$iPr | H | H | H | H | Br |

1-Methylethyl 5-[(2-bromobenzoyl)amino]-2-chlorobenzoate
M.P. °C.: 123–140

| 86 | H | Cl | CO$_2$ET | H | H | H | H | OCH$_3$ |

Ethyl 2-chloro-5-[(2-methoxybenzoyl)amino]benzoate
M.P. °C.: 56–57

| 87 | H | Cl | CO$_2$Et | H | H | H | H | H |

Ethyl 5-(benzoylamino)-2-chlorobenzoate
M.P. °C.: 140–142

| 88 | H | Cl | CO$_2$iPr | H | H | H | H | NH$_2$ |

Ethyl 5-[(2-aminobenzoyl)amino]-2-chlorobenzoate
M.P. °C.: 150–152

| 89 | H | Cl | CO$_2$iPr | H | H | H | H | H |

1-Methylethyl 5-(benzoylamino)-2-chlorobenzoate
M.P. °C.: 105–107

| 90 | H | Cl | CO$_2$iPr | H | H | H | H | Cl |

1-Methylethyl 2-chloro-5-[(2-chlorobenzoyl)amino]benzoate
M.P. °C.: 100–101

| 114 | H | Cl | CO$_2$iPr | H | H | H | H | NH COCN$_3$ |

1-Methylethyl 5-[(2-acetamidobenzoyl)amino]-2-chlorobenzoate
M.P. °C.: 130–132

| 146 | H | Cl | CO$_2$iPr | H | H | H | H | NH CO$_2$ET |

M.P. °C.: 150–151

| 159 | H | Cl | CO$_2$iPr | H | H | H | H | NH$_2$HCL |

M.P. °C.: 226–229

Dithiins

[Structure: 5,6-dihydro-3-methyl-1,4-dithiin-2-carboxamide with phenyl bearing R$^2$ and R$^3$ substituents]

| Compound | R$^2$ | R$^3$ |
|---|---|---|
| 26 | Cl | H |

N-(4-Chlorophenyl)-5,6-dihydro-3-methyl-1,4-dithiin-2-carboxamide

| 27 | Cl | CO$_2$iPr |

1-Methylethyl 2-chloro-5[[(5,6-dihydro-3-methyl-1,4-dithiin-2-yl)carbonyl]amino]benzoate

Dioxins

TABLE I-continued
Compounds Prepared

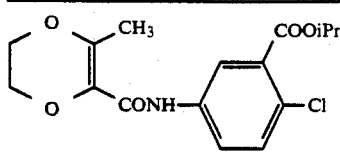

Compound 28  1-Methylethyl 2-chloro-5-[[(5,6-dihydro-3-methyl-1,4-dioxin-2-yl)carbonyl]amino]benzoate

Pyrans

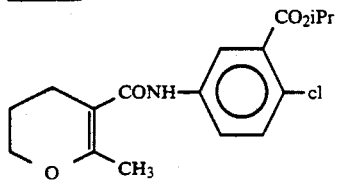

115  1-Methylethyl 2-chloro-5-[[(3,4-dihydro-6-methyl-2H-pyran-5-yl)carbonyl]amino]benzoate
M.P. °C.: 147-148

Acyclic Derivatives

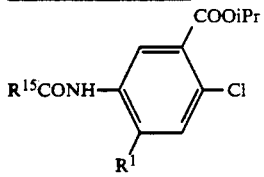

| Compound | R$^1$ | R$^{15}$ |
|---|---|---|
| 91 | H | $(CH_3)_2C=CH-$ |

1-Methylethyl 2-chloro-5-[(3-methyl-1-oxo-2-butenyl)amino]-benzoate
M.P. °C.: 98-99

| 92 | H | $CH\equiv C-CH_2-$ |

1-Methylethyl 2-chloro-5-[((2-propynyloxy)carbonyl]amino]benzoate
M.P. °C.: 120-122

| 93 | H | nBuO— |

1-Methylethyl 5-[(butoxycarbonyl)amino]-2-chlorobenzoate
M.P. °C.: 85-87

| 29 | H | iPrO |

1-Methylethyl 2-chloro-5-[[1-methylethoxycarbonyl]amino]benzoate
M.P. °C.: 108-109

| 30 | F | t-Bu |

1-Methylethyl 2-chloro-5-[(2,2-dimethyl-1-oxopropyl)amino]-4-fluorobenzoate
M.P. °C.: 81-83

The following supplemental Table I's list additional compounds that were prepared and are within the scope of this invention. Specific examples following the Tables describe in detail the exact procedures for the preparation of certain of the compounds in the Tables; the balance being prepared by similar processes.

TABLE IA
PREPARED COMPOUNDS

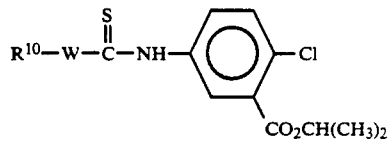

| COMPOUND | W | R$^{10}$ | M.P. °C. |
|---|---|---|---|
| 31 | 0 | $CH_3$ | 108-110 |
| 32 | 0 | $CH(CH_3)_2$ | 89-90 |
| 33 | 0 | $CH_2CH_3$ | 65-66 |

TABLE IA-continued
PREPARED COMPOUNDS

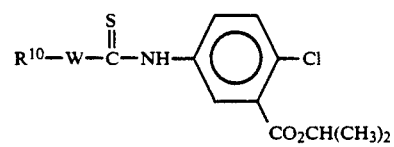

| COMPOUND | W | R$^{10}$ | M.P. °C. |
|---|---|---|---|
| 34 | 0 | $CH_2(CH_2)_2CH_3$ | OIL |
| 35 | 0 | $CH_2(CH_2)CH_3$ | 78-80 |
| 36 | 0 | $CH_2(CH_2)_3CH_3$ | OIL |
| 37 | 0 | $CH_2CH=CH_2$ | OIL |
| 39 | 0 | 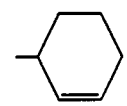 | OIL |

TABLE IA-continued
PREPARED COMPOUNDS

R^10—W—C(=S)—NH—[phenyl with Cl and CO2CH(CH3)2]

| COMPOUND | W | R^10 | M.P. °C. |
|---|---|---|---|
| 42 | O | CH2-furyl | 66–68 |
| 43 | O | CH2-tetrahydrofuryl | OIL |
| 44 | O | C6H11 (CYCLO) | 94–95 |
| 46 | O | CH2C3H5 (CYCLO) | 77–78 |
| 47 | O | CH2CH2OCH3 | OIL |
| 48 | NCH3 | CH3 | 72–74 |
| 49 | NH | CH(CH3)2 | 130–132 |
| 116 | O | CH2CF3 | 97–99 |
| 117 | O | CH2C6H5 | 74–76 |
| 118 | O | 2-ADAMANTYL | 138–142 |
| 119 | O | 1-ADAMANTYL | 168–169 |
| 120 | O | 3-methyloxetanyl-CH2 | 108–110 |
| 121 | O | CH2CH2SCH3 | 95–96 |
| 122 | O | 4-(OC2H5)C6H4-CH=CHCH3 | OIL |

TABLE IB
PREPARED COMPOUNDS (CH3)2CH—O—C(=S)—NH—[phenyl with Cl and CO2R^5]

| COMPOUND | R^5 | M.P. °C. |
|---|---|---|
| 132 | CH2OCOC(CH3)3 | OIL |
| 133 | CH(CF3)2 | 109–110 |
| 134 | C(CH3)3 | OIL |
| 135 | CH2OCOC6H4-2-CH3 | 88–89 |
| 136 | CH2CF3 | 87–90 |
| 137 | CH2CH2OCOCH3 | OIL |
| 138 | CH2C≡CH | 75–83 |
| 139 | C6H5 | 106–107 |
| 140 | C6H4-2-CH3 | 93–94 |
| 141 | CH2CH2Si(CH3)3 | 89–92 |
| 142 | CH2C3H5(CYCLO) | 62–64 |
| 143 | CH2CHC4H9 / C2H5 | OIL |
| 144 | CH2C6H5 | 88–89 |

TABLE IB-continued
PREPARED COMPOUNDS (CH3)2CH—O—C(=S)—NH—[phenyl with Cl and CO2R^5]

| COMPOUND | R^5 | M.P. °C. |
|---|---|---|
| 148 | CH2CH3 | 72–73 |
| 149 | CH2iPr | OIL |
| 151 | CH(ET)2 | 85–86 |
| 152 | CH(CH3)ET | 60–62 |
| 153 | nBu | OIL |
| 154 | nPr | 57–58 |
| 155 | CH2CH(ET)2 | OIL |

TABLE IC
PREPARED COMPOUNDS

R^18—Y^3—C(SR^a)=N—[phenyl with Cl and CO2iPr]

| COMPOUND | Y^3 | R^18 | R^a | M.P. °C. |
|---|---|---|---|---|
| 50 | O | CH(CH3)2 | CH3 | OIL |
| 51 | O | CH(CH3)2 | CH2CH3 | OIL |
| 52 | O | CH(CH3)2 | CH2CH2CH3 | OIL |

TABLE ID
PREPARED COMPOUNDS

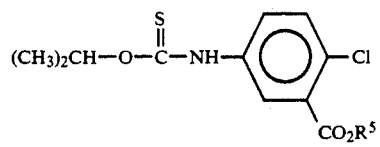

| COMPOUND | R^7 | R^8 | M.P. °C. |
|---|---|---|---|
| 58 | CH3 | CH3 | 109–110 |
| 59 | H | H | 83–85 |
| 60 | H | CH3 | 125–126 |

TABLE IE
PREPARED COMPOUNDS

[phenyl-R^14]—C(=S)—NH—[phenyl with R^4, R^2, CO2R^a]

| COMPOUND | R^a | R^14 | R^2 | R^4 | M.P. °C. |
|---|---|---|---|---|---|
| 61 | CH(CH3)2 | H | Cl | H | 93–94 |
| 62 | CH2CH3 | H | Cl | H | 125–127 |
| 63 | CH(CH3)2 | H | F | F | 92–93 |
| 64 | CH(CH3)2 | CH3 | Cl | H | 110–111 |
| 65 | CH(CH3)2 | OCH3 | Cl | H | 79–80 |
| 123 | C6H11(CYCLO) | OCH3 | CL | H | 82–84 |
| 124 | C5H9(CYCLO) | OCH3 | Cl | H | 85–86 |
| 125 | C6H11(CYCLO) | Cl | Cl | H | 105–106 |
| 126 | C5H9(CYCLO) | H | Cl | H | 114–115 |

TABLE IE-continued
PREPARED COMPOUNDS

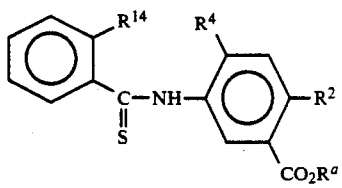

| COMPOUND | $R^a$ | $R^{14}$ | $R^2$ | $R^4$ | M.P. °C. |
|---|---|---|---|---|---|
| 127 | $C_6H_{11}$(CYCLO) | H | Cl | H | 90–91 |

TABLE IF

| PREPARED COMPOUNDS | | m.p. °C. |
|---|---|---|
| 67 | (3-methyl-but-2-enethioamide, N-(4-chloro-3-isopropoxycarbonylphenyl)) | 85–86 |

$R^H$ in the following is 5-($CO_2iPr$)-2-Cl-phenyl

| 94 | (N-isopropylthio-methyl-propanamide with $CONHR^H$) | 115–117 |
| 98 | (2-methoxyphenyl-NH-C(=NH)-NH-(4-chloro-3-cyclopentyloxycarbonylphenyl)) | 172–173 |
| 99 | (2-methoxyphenyl-NH-C(=O)-NH-$R^H$) | 175–177 |
| 102 | (cyclohexyl-S, O-C(=O)-NHR$^H$) | 145–146 |
| 103 | (2-methyl-5-phenyl-oxazole-4-CONHR$^H$) | 117–119 |
| 104 | (indole-2-CONHR$^H$) | 207–210 |
| 105 | (2-methyl-4-phenyl-oxazole-5-CONHR$^H$) | 131–132 |

TABLE IF-continued

| PREPARED COMPOUNDS | | m.p. °C. |
|---|---|---|
| 106 | 3-Me-thiophene-2-CONHR$^H$ | 102–104 |
| 107 | cyclohex-1-ene-1-CONHR$^H$ | 90–91 |
| 108 | 3-Me-5-Me-thiophene-2-CONHR$^H$ | 110–112 |
| 109 | thiophene-3-CONHR$^H$ | 120–121 |
| 128 | 3-Me-5-Me-thiophene-2-CSNHR$^H$ | 117–118 |
| 129 | 3-Me-thiophene-2-CONH-(4-Cl, 3-CO$_2$C$_6$H$_{11}$(Cyclo))-phenyl | 110–111 |
| 130 | 2-CO$_2$Me-C$_6$H$_4$-SO$_2$NHCONHR$^H$ | 98–100 |
| 131 | C$_6$H$_5$-SO$_2$N=C(2-F-C$_6$H$_4$)-NHR$^H$ | 178–180 |
| 145 | iPrO-C(=S)-NH-(3-CO$_2$Et, 4-SMe)-C$_6$H$_3$ | 101–106 |
| 150 | iPrO-C(=S)-NH-(3-CO$_2$Et, 4-Me)-C$_6$H$_3$ | 112–114 |
| 156 | (EtO)$_2$P(=S)-NHR$^H$ | OIL |

EXAMPLE 1

A. Preparation of 1-Methylethyl 5-amino-2-chlorobenzoate

Methanesulfonic acid (99%, 318 g, 3.3 mole) was added slowly to a stirred mixture of 5-amino-2-chlorobenzoic acid (85%, 215 g, 1.1 mole) in 2-propanol (about 1100 ml). The mixture was heated under reflux with stirring for 6 hours, then the excess 2-propanol was evaporated under reduced pressure. Water (about 1000 ml) was added to the residue and the mixture was neutralized with solid sodium bicarbonate and extracted with methylene chloride (about 1200 ml). The extract was washed twice with water, dried over magnesium sulfate and evaporated to give a purple oil, which crystallized on seeding. The product was reprecipitated from dilute hydrochloric acid solution by slowly basifying with concentrated ammonium hydroxide and seeding. The resulting crystals after drying melted at 50.5°–52° C. (170 g, 75% yield).

B. Preparation of 1-Methylethyl 2-chloro-5-[[(5,6-dihydro-2-methyl-1,4-oxathiin-3-yl)carbonyl]amino]benzoate (Compound 1)

Ethyl 5,6-dihydro-2-methyl-1,4-oxathiin-3-carboxylate was prepared by the method of U.S. Pat. No. 3,249,499 (col. 5, lines 36–55), with the following modifications: toluene was used as the solvent instead of benzene, sodium bicarbonate was used as the base instead of potassium hydroxide, and the azeotropic removal of water was carried out under reduced pressure at about 65° C. 5,6-Dihydro-2-methyl-1,4-oxathiin-3-carboxylic acid was prepared by hydrolysis of the ester as described in the 5 same patent (col. 5, lines 56-68, where the acid is named 2,3-dihydro-5-carboxy-6-methyl-1,4-oxathiin).

Thionyl chloride (6.5 g, 0.055 mole) was added to a stirring slurry of 5,6-dihydro-2-methyl-1,4-oxathiin-3-carboxylic acid (8.0 g, 0.050 mole) in methylene 10 chloride (50 ml). The mixture was stirred at 35°–40° C. for 4 hours, during which the solid completely dissolved. The solution was then evaporated under reduced pressure at about 35° C. to remove hydrogen chloride, sulfur dioxide and unreacted thionyl chloride. The residue, crude 5,6-dihydro-2-methyl-1,4-oxathiin-3-carbonyl chloride, which solidified, was dissolved in methylene chloride (50 ml). The solution was chilled in ice and treated dropwise with a solution of 1-methylethyl 5-amino-2-chlorobenzoate (10.7 g, 0.050 mole) and triethylamine (5.5 g, 0.055 mole) in methylene chloride (50 ml). The addition was carried out over about 2 hours, after which the reaction mixture was left stirring overnight at room temperature.

The reaction mixture was worked up by washing the methylene chloride solution with water (50 ml), dilute hydrochloric acid (3.5%, 50 ml), water (50 ml), dilute sodium hydroxide (2%, 25 ml) and water (50 ml). The methylene chloride solution was then filtered through anhydrous sodium sulfate (about 5 g) and evaporated. The residue solidified. The crude product (17.0 g, m.p. 123°–128° C.) was recrystallized from 95% ethanol (175 ml) to give light tan crystals, m.p. 130°–132° C. (12.9 g, 72.5% yield).

Analysis: Calc.: C 54.01, H 5.10, N 3.94, Found: C 53.96, H 4.98, N 3.94

NMR (CDCl$_3$): 1.4(6H,d), 2.3(3H,s), 2.95 (2H,m), 4.35 (2H,m), 5.2 (1H,m), 7.2–8.0 (3H,m), 8.2 (1H,bs)

C. Alternate Preparation

A solution of diketene (4.0 g, 0.048 mole) in toluene (20 ml) was added dropwise over 1.5 hours to a cooled (8°–12° C.) solution of 1-methylethyl 5-amino-2-chlorobenzoate (9.9 g, 0.046 mole) in toluene (20 ml). The reaction mixture was warmed slowly to 40° C., then to 60°–65° C. for 4 hours. The reaction mixture was washed with dilute hydrochloric acid and twice with water, filtered and evaporated. The residue, a viscous purple oil, slowly solidified. The product, crude 1-methylethyl 2-chloro-5-[(1,3-dioxobutyl)amino]benzoate (11.7 g), melted at about 72-75° C. Recrystallization of a sample (1.0 g) from toluene (5 ml) gave an off white solid, m.p. 89°–91° C. (0.5 g).

Crude 1-methylethyl 2-chloro-5-[(1,3-dioxobutyl)amino]benzoate (10.0 g, 0.034 mole) was stirred in toluene (50 ml) and treated dropwise at room temperature with a solution of sulfuryl chloride (4.6 g, 0.034 mole) in toluene (20 ml). Stirring was continued overnight, then the mixture was evaporated under reduced pressure. The residue failed to crystallize, but its NMR spectrum was consistent with 1-methylethyl 2-chloro-5-[(2-chloro-1,3-dioxobutyl)amino]benzoate, about half in the enol form.

2-Mercaptoethanol (2.6 g, 0.033 mole) was added to a solution of crude 1-methylethyl 2-chloro-5-[(2-chloro-1,3-dioxobutyl)amino]benzoate (11 g) in toluene (75 ml). Sodium bicarbonate (5.0 g, 0.06 mole), incompletely dissolved in water (40 ml), was added over 30 minutes with rapid stirring. Stirring was continued for another hour, then the toluene layer was separated, washed with water, and filtered. p-Toluenesulfonic acid (0.2 g, dehydration catalyst) was added to the toluene solution, which was heated to reflux at 60°–70° C. under reduced pressure, using a Dean-Stark trap to remove water. After water ceased being formed, the toluene solution was cooled and washed first with water, then with 2% aqueous sodium bicarbonate and again with water. Evaporation of the toluene gave a viscous oil. Crystallization from 90% ethanol (30ml) gave an off-white solid, m.p. 127°–130° C. (1.2 g, 10% yield), which was identified (mixed m.p., NMR spectra) as 1-methylethyl 2-chloro-5-[[(5,6-dihydro-2-methyl-1,4-oxathiin-3-yl)carbonyl]amino]benzoate.

EXAMPLE 2

1-Methylethyl 2-chloro-5-[[(5,6-dihydro-2-methyl-1,4-oxathiin-3-yl)carbonyl]amino]-4-fluorobenzoate (Compound 2)

Thionyl chloride (4.2 g, 0.035 mole) was added to a stirring slurry of 5,6-dihydro-2-methyl-1,4-oxathiin-3-carboxylic acid 4.8 g, 0.030 mole) in methylene chloride (40 ml). The mixture was warmed to 35° C. for 3 hours, then left stirring overnight at room temperature. The solution was then evaporated under reduced pressure at about 35° C. The solid residue, crude 5,6-dihydro-2-methyl-1,4-oxathiin-3-carbonyl chloride, was dissolved in methylene chloride (50 ml) and the solution chilled in ice and treated dropwise with a solution of 1-methylethyl 5-amino-2-chloro-4-fluorobenzoate (7.0 g, 0.030 mole) and triethylamine (3.5 g, 0.035 mole) in methylene chloride (50 ml). The addition was carried out over 2 hours, after which the reaction mixture was stirred at 20°–35° C. for 3 hours.

The reaction mixture was worked up by washing the methylene chloride solution first with water (50 ml), then with dilute hydrochloric acid 3.5%, 50 ml), again with water (50 ml), then with dilute sodium hydroxide (2%, 25 ml) and a final wash with water (50 ml). The methylene chloride solution was then evaporated to give an oil, which solidified. The crude product was recrystallized from ethanol (100 ml) to give crystals, m.p. 123°-125° C. (8.2 g, 73% yield).

Analysis: Calc.: C 51.41, H 4.58, N 3.75, Found: C 50.91, H 4.45, N 3.43

NMR: (CDCl$_3$) : 1.35 (6H,d), 2.3 (3H,s , 3.0 (2H,m), 4.4 (2H,m), 5.2 (1H,m), 7.2 (1H,d), 8.2 (1H,bs), 8.8 (1H,d)

EXAMPLE 3

Methyl 2-chloro-5[[(5,6-dihydro-2-methyl-1,4-oxathiin-3-yl)carbonyl]amino]benzoate (Compound 3)

Thionyl chloride (4.1 g, 0.034 mole) was added to a stirred mixture of 5,6-dihydro-2-methyl-1,4-oxathiin-3-carboxylic acid (4.3 g, 0.027 mole) and methylene chloride (35 ml). The mixture was warmed to a gentle reflux for about 3.5 hours, left stirring overnight at room temperature, and then evaporated under reduced pressure. The solid residue, crude 5,6-dihydro-2-methyl-1,4-oxathiin-3-carbonyl chloride, was dissolved in methylene chloride (50 ml) and the solution treated dropwise at 5°-10° C. over 2 hours with a solution of methyl 5-amino-2-chlorobenzoate (5.1 g, 0.027 mole) and triethylamine (3.1 g, 0.031 mole) in methylene chloride (35 ml). The reaction mixture was stirred at room temperature for a further 3 hours and worked up by washing in sequence with water (50 ml), dilute hydrochloric acid (3.5%, 50 ml), water (50 ml), dilute sodium hydroxide (2%, 25 ml) and water (50 ml). The methylene chloride was then evaporated to leave an oil (8.2 g), which slowly solidified. Recrystallization from methanol (75 ml) gave a beige solid, m.p. 115°-117° C. (5.5 g, 62.5% yield).

Analysis: Calc.: C 51.30, H 4.31, N 4.27, Found: C 50.96, H 4.25, N 4.23

NMR: (CDCl$_3$) : 2.3 (3H,s), 3.0 (2H,m), 3.9 (3H,s), 4.4 (2H,m), 7.2-8.2 (4H,m)

EXAMPLE 4

Ethyl 2-chloro-5-[[(5,6-dihydro-2-methyl-1,4-oxathiin-3-yl)-carbonyl]amino]benzoate (Compound 4)

Thionyl chloride (7.3 g, 0.055 mole) was added to a stirred mixture of 5,6-dihydro-2-methyl-1,4,oxathiin-3-carboxylic acid (8.0 g, 0.050 mole) and methylene chloride (50 ml). The mixture was warmed to 35° C. for 4.5 hours, then evaporated under reduced pressure. The solid residue, crude 5,6-dihydro-2-methyl-1,4-oxathiin-3-carbonyl chloride, was dissolved in methylene chloride (50 ml) and the solution treated dropwise at 5°-10° C. over 5 hours with a solution of ethyl 5-amino-2-chlorobenzoate (10.0 g, 0.050 mole) and triethylamine (5.5 g, 0.054 mole) in methylene chloride (50 ml). The reaction mixture was left stirring overnight at room temperature.

The reaction mixture was worked up by washing the methylene chloride solution in sequence with water (50 ml), dilute hydrochloric acid (3.5%, 50 ml), water (50 ml), dilute sodium hydroxide (2%, 25 ml and water (50 ml). The methylene chloride solution was filtered through anhydrous sodium sulfate and evaporated. The residual brown oil, which slowly crystallized, was recrystallized from 95% ethanol (80 ml to give a tan product, m.p. 86°-88° C. 10.6 g, 62% yield).

Analysis: Calc.: C 52.71, H 4.72, N 4.10, Found: C 53.10, H 4.97, N 4.05

NMR: (CDCl$_3$) : 1.4 (3H,t), 2.3 (3H,s), 3.0 2H,m), 4.2-4.6 (4H,m), 7.2-7.95 (3H,m), 8.05 (1H,bs)

EXAMPLE 5

Propyl 2-chloro-5-[[(5,6-dihydro-2-methyl-1,4-oxathiin-3-yl)-carbonyl]amino]benzoate (Compound 5)

Thionyl chloride (4.4 g, 0.037 mole) was added to a stirred mixture of 5,6-dihydro-2-methyl-1,4-oxathiin-3-carboxylic acid (5.25 g, 0.033 mole) and methylene chloride (50 ml). The mixture was warmed to a gentle reflux for 3 hours, stirred overnight at room temperature, and evaporated under reduced pressure. The solid residue, crude 5,6-dihydro-2- methyl-1,4-oxathiin-3-carbonyl chloride, was dissolved in methylene chloride (50 ml), chilled, and treated dropwise over about 2 hours with a solution of propyl 5-amino-2-chlorobenzoate (7.0 g, 0.033 mole) and triethylamine (3.5 g, 0.035 mole) in methylene chloride (50 ml).

The reaction mixture was stirred overnight at room temperature, and worked up by washing in sequence with water (50 ml), dilute hydrochloric acid (3.5%, 50 ml), water (50 ml), dilute sodium hydroxide (2%, 25 ml) and water (50 ml). The methylene chloride was then evaporated to give a brown oil (8.2 g), which crystallized slowly. Recrystallization from 100% ethanol (60 ml) gave tan crystals, m.p. 76°-78° C. (6.2 g, 53% yield).

Analysis: Calc.: C 54.01, H 5.10, N 3.94, Found: C 53.99, H 5.06, N 3.59

NMR: (CDCl$_3$) : 1.0 (3H,t), 1.8 (2H,m), 2.3 (3H,s), 3.0 (2H,m), 4.15-4.55 (4H,m), 7.2-8.0 (3H,m), 8.1 (1H,bs)

EXAMPLE 6

Butyl 2-chloro-5-[[(5,6-dihydro-2-methyl-1,4-oxathiin-3-yl)carbonyl]aminobenzoate (Compound 6)

Thionyl chloride (4.4 g, 0.037 mole) was added to a stirred mixture of 5,6-dihydro-2-methyl-1,4-oxathiin-3-carboxylic acid (5.0 g, 0.031 mole) and methylene chloride (50 ml). The mixture was warmed to 35°-40° C. for about 3 hours, left stirring overnight at room temperature, and evaporated under reduced pressure. The solid residue, crude 5,6-dihydro-2-methyl-1,4-oxathiin-3-carbonyl chloride, was dissolved in methylene chloride (50 ml) and the solution treated dropwise at 5°-10° C. over 2 hours with a solution of butyl 5-amino-2-chlorobenzoate (6.1 g, 0.031 mole) and triethylamine (3.6g, 0.036 mole) in methylene chloride (50 ml). The reaction mixture was stirred at room temperature for a further 3 hours and then worked up by washing in sequence with water (50 ml), dilute hydrochloric acid (3.5%, 50 ml), water (50 ml), dilute sodium hydroxide (2%, 25 ml) and water (50ml). Evaporation of the solvent left an oil, which slowly solidified. Recrystallization from methanol (50 ml) gave beige crystals, m.p. 71°-73° C. (4.7 g, 41% yield).

Analysis: Calc.: C 55.21, H 5.45, N 3.79, Found: C 55.10, H 5.42, N 3.51

NMR: (CDCl$_3$) : 1.0 (3H,m), 1.2-2.0 (4H,m), 3.0 (2H,m), 4.15-4.55 (4H,m), 7.2-7.95 (3H,m), 81 (1H,bs)

EXAMPLE 7

1-Methylethyl 2-chloro-5-[[(2-ethyl-5,6-dihydro-1,4 oxathiin-3-yl)carbonyl]amino]benzoate (Compound 7)

Thionyl chloride (3.7 g, 0.031 mole, was added to a stirred mixture of 2-ethyl-5,6-dihydro-1,4-oxathiin-3-carboxylic acid (5.0 g, 0.029 mole) and methylene chloride (35 ml). The mixture was warmed to about 35° C. for 4 hours and then evaporated under reduced pressure. The dark residue, crude 2-ethyl-5,6-dihydro-1,4-oxathiin-3-carbonyl chloride, was dissolved in methylene chloride (50 ml) and treated dropwise at about 10×C over 2.5 hours with a solution of 1-methylethyl 5-amino-2-chloro benzoate (6.1 g, 0.029 mole) and triethylamine (3.3 g, 0.033 mole) in methylene chloride (50 ml). The reaction mixture was stirred overnight at room temperature and worked up by washing in sequence with water (50 ml), dilute hydrochloric acid (3.5%, 50 ml), water (50 ml), dilute sodium hydroxide (2%, 25 ml) and water (50 ml). The methylene chloride was then evaporated to give a solid residue (10.5 g). Recrystallization from 100% ethanol (40 ml) gave a grey-brown solid, m.p. 90°-92° C. (5.0 g, 47% yield).

NMR: ($CDCl_3$) : 1.15 (3H,t), 1.37 (6H,d), 2.6 (2H,quartet), 3.0 (2H,m), 4.4 (2H,m), 5.25 (1H,m), 7.25-7.95 (3H,m), 8.1 (1H,bs)

EXAMPLE 8

Ethyl 3-[[(5,6-dihydro-2-methyl-1,4-oxathiin-3-yl)carbonyl]amino]benzoate (Compound 8)

Thionyl chloride (6.5 g, 0.055 mole) was added to a stirred mixture of 5,6-dihydro-2-methyl-1,4-oxathiin-3-carboxylic acid (8.0 g, 0.050 mole) and methylene chloride (50 ml). The mixture was warmed to 35°-40° C. for hours and the resulting dark solution evaporated under reduced pressure. The solid residue, crude 5,6-dihydro-2-methyl-1,4-oxathiin-3-carbonyl chloride, was dissolved in methylene chloride (50 ml). On the following day, the solution was treated dropwise at 5°-20° C. over 2 hours with a solution of ethyl 3-aminobenzoate (8.2 g, 0.050 mole) and triethylamine (5.5 g, 0.054 mole) in methylene chloride (50 ml). The reaction mixture was stirred at room temperature for a further 5 hours and worked up by washing in sequence with water (50 ml), dilute hydrochloric acid (3.5%, 50 ml), water (50 ml), dilute sodium hydroxide (2%, 25 ml) and water (50 ml). Evaporation of the solvent left an oil, which slowly solidified. Recrystallization from ethanol 75 ml gave yellow-tan crystals, m.p. 100°-102° C. (11.2 g, 73% yield).

Analysis: Calc.: C 58.62, H 5.57, N 4.56, Found: C 58.46, H 5.74, N 4.72

NMR: ($CDCl_3$) : 1.4 (3H,t), 2.3 (3H,s), 3.0 (2H,m), 4.15-4.6 (4H,m), 7.2-8.3 (5H,m)

EXAMPLE 9

N-(3-Cyanophenyl)-5,6-dihydro-2-methyl-1,4-oxathiin-3 carboxamide (Compound 9)

5,6-Dihydro-2-methyl-1,4-oxathiin-3-carboxylic acid (5.0 g, 0.031 mole) and thionyl chloride (4.1 g, 0.034 mole) were heated under reflux in methylene chloride for about 2 hours, then evaporated under reduced pressure. The solid residue, crude 5,6-dihydro-2-methyl-1,4-oxathiin-3-carbonyl chloride, was dissolved in methylene chloride and the chilled solution treated dropwise with a solution of 3-aminobenzonitrile (3.7 g, 0.031 mole) and triethylamine (3.2 g, 0.032 mole) in methylene chloride. The reaction mixture was stirred at room temperature for a further 3 hours and then worked up by washing with dilute hydrochloric acid and dilute sodium hydroxide. Evaporation of the solvent gave a solid residue, which was recrystallized from methanol to give a white solid, m.p. 119°-121° C. (5.5 g, 67% yield).

NMR: ($CDCl_3$) : 2.3 (3H,s), 3.0 (2H,m), 4.4 (2H,m), 7.2-8.2 (5H,m)

EXAMPLE 10

1-Methylethyl 5-[[(5,6-dihydro-2-methyl-1,4-oxathiin-3-yl)carbonyl]amino]benzoate (Compound 10)

Thionyl chloride (3.5 g, 0.029 mole) was added to a stirred mixture of 5,6-dihydro-2-methyl-1,4-oxathiin-3-carboxylic acid (4.7 g, 0.029 mole) and methylene chloride (100 ml). The mixture was warmed to 30°-35° C. for 4 hours, then evaporated under reduced pressure. The residue, crude 5,6-dihydro-2-methyl-1,4-oxathiin-3-carbonyl chloride, was dissolved in methylene chloride (100 ml), and the ice-chilled solution treated dropwise with a solution of 1-methylethyl 3-aminobenzoate (5,.2 g, 0.029 mole) and triethylamine (2.9 g, 0.029 mole) in methylene chloride (50 ml). The reaction mixture was stirred overnight at room temperature and then worked up by washing in sequence with water, dilute hydrochloric acid, water, 2% sodium hydroxide and water. Evaporation of the solvent left an oil, which solidified. After recrystallization from ethanol (30 ml) the product (4.0 g, 42% yield) melted at 92°-94° C. Analysis: Calc.: C 59.79, H 5.96, N 4.36, Found: C 59.46, H 6.21, N 4.51

NMR: ($CDCl_3$) : 1.35 (6H,d), 2.3 (3H,s) 3.0 (2H,m), 4.4 (2H,m), 4.4 (2H,m), 5.25 (1H,m), 7.2-8.2 (5H,m)

EXAMPLE 11

Ethyl 2-chloro-5-[[(2-ethyl-5,6-dihydro-1,4-oxathiin-3-yl)carbonyl]amino]benzoate (Compound 11)

Thionyl chloride (4.0 g, 0.034 mole) was added to a stirred mixture of 2-ethyl-5,6-dihydro-1,4-oxathiin-3-carboxylic acid (5.9 g, 0.034 mole) and methylene chloride (100 ml). The mixture was warmed to about 35° C. for 3 hours, then evaporated under reduced pressure. The residue, crude 2-ethyl-5,6-dihydro-1,4-oxathiin-3-carbonyl chloride, was dissolved in methylene chloride (100 ml), and the ice-chilled solution treated dropwise with a solution of ethyl 5-amino-2-chlorobenzoate (6.8 g, 0.034 mole) and triethylamine (3.7 g, 0.037 mole) in methylene chloride (100 ml). The reaction mixture was stirred overnight at room temperature and then worked up by washing in sequence with water, dilute hydrochloric acid, water, 2% sodium hydroxide and water. Evaporation of the solvent left an oil, which solidified. After recrystallization from ethanol (30 ml) the product (7.0 g, 58% yield) melted at 86°-88° C.

Analysis: Calc.: C 54.01, H 5.10, N 3.94, Found: C 53.60, H 5.03, N 4.04

NMR: ($CDCl_3$) : 1.0-1.6 (6H,m) 2.6 (2H,quartet), 3.0 (2H,m), 4.15-4.6 (4H,m), 7.2-7.9 (3H,m), 8.05 (1H,bs)

EXAMPLE 12

1-Methylethyl 5-[[(5,6-dihydro-2-methyl-1,4-oxathiin-3-yl)carbonyl]amino]-4-fluoro-2-methylbenzoate (Compound 12)

Thionyl chloride (4.7 g, 0.040 mole was added to a stirred mixture of 5,6-dihydro-2-methyl-1,4-oxathiin-3-carboxylic acid (6.0 g, 0.037 mole) and methylene chloride (50 ml). The mixture was stirred overnight at room temperature, then evaporated under reduced Pressure. The solid residue, crude 5,6-dihydro-2-methyl-1,4-oxathiin-3-carbonyl chloride, was dissolved in methylene chloride (50 ml) and the chilled solution treated dropwise over about 1 hour with a solution of 1-methylethyl 5-amino-4-fluoro-2-methylbenzoate (7.9 g, 0.037 mole) and triethylamine (3.9 g, 0.039 mole) in methylene chloride (50 ml). The reaction mixture was left stirring overnight at room temperature and worked up by washing in sequence with water (50 ml), dilute hydrochloric acid (3.5%, 50 ml), water (50 ml), dilute sodium hydroxide (2%, 25 ml) and water (50 ml). Evaporation of the solvent left a solid residue. Recrystallization from 100% ethanol (60 ml) gave yellow-tan crystals, m.p. 119°–122° C. (7.6 g, 57% yield).

Analysis: Calc.: C 57.78, H 5.70, N 3.96, Found: C 57.75, H 5.79, N 3.99

NMR: (CDCl$_3$) : 1.35 (6H,d), 2.3 (3H,s), 2.55 (3H,s), 3.0 2H,m), 4.4 (2H,m), 5.2 (1H,s), 6.95 (1H,d), 8.1 (1H,bs), 8.75 (1H,d)

EXAMPLE 13

1-Methylethyl 3-[[(5,6-dihydro-2-methyl-1,4-oxathiin-3-yl)carbonyl]amino-4-fluorobenzoate (Compound 13)

Thionyl chloride (4.6 g, 0.039 mole) was added to a stirred mixture of 5,6-dihydro-2-methyl-1,4-oxathiin-3-carboxylic acid (6.0 g, 0.037 mole) and methylene chloride (50 ml). The mixture was warmed to 35°–40° C. for about 3 hours, then evaporated under reduced pressure. The residue, crude 5,6-dihydro-2-methyl-1,4-oxathiin-3-carbonyl chloride, was dissolved in methylene chloride (50 ml) and the ice-cooled solution treated dropwise with a solution of 1-methylethyl 3-amino-4-fluorobenzoate (7.4 g, 0.037 mole) and triethylamine (3.9 g, 0.039 mole) in methylene chloride (50 ml). The reaction mixture was stirred overnight at room temperature, and then washed in sequence with water (50 ml), dilute hydrochloric acid (3.5%, 50 ml), water (50 ml), dilute sodium hydroxide (2%, 25 ml) and water (50 ml), dried with anhydrous sodium sulfate and evaporated. Recrystallization of the solid residue from 100% ethanol (100 ml) gave light brown crystals, m.p. 132°–135° C. (7.8 g, 61% yield).

Analysis: Calc.: C 56.63, H 5.35, N 4.13, Found: C 56.40, H 5.26, N 4.25

NMR: (CDCl$_3$) : 1.35 (6H,d), 2.3 (3H,s), 3.0 (2H,m), 4.4 (2H,m), 5.25 (1H,m), 7.1 (1H,m), 7.8 (1H,m) 8.2 (1H,bs), 8.9 (1H,m)

EXAMPLE 14

Ethyl 3-[[(5,6-dihydro-2-methyl-1,4-oxathiin-3-yl)carbonyl]amino]-4-methylbenzoate (Compound 14)

Thionyl chloride (4.5 g, 0.038 mole) was added to a stirred mixture of 5,6-dihydro-2-methyl-1,4-oxathiin-3-carboxylic acid (6.0 g, 0.037 mole) and methylene chloride (100 ml . The mixture was warmed to 30°–35° C. for 3 hours, then evaporated under reduced pressure. The residue, crude 5,6-dihydro-2-methyl-1,4-oxathiin-3-carbonyl chloride, was dissolved in methylene chloride (100 ml), and the ice-chilled solution treated dropwise with a solution of ethyl 3-amino-4-methylbenzoate (6.7 g, 0.037 mole) and triethylamine (4.0 g, 0.040 mole) in methylene chloride (100 ml). The reaction mixture was stirred overnight at room temperature and then worked up by washing in sequence with water, dilute hydrochloric acid, water, 2% sodium hydroxide and water. Evaporation of the solvent gave an oil, which solidified. After recrystallization from ethanol (30 ml), the product (7.1 g, 59% yield) melted at 105°–107° C.

Analysis: Calc.: C 59.79, H 5.96, N 4.36, Found: C 59.87, H 5.73, N 4.52

NMR: (CDCl$_3$) : 1.35 (3H,t), 2.25 (3H,s), 2.3 (3H,s) 2.3 (3H,s), 3.0 (2H,m), 4.15–4.55 (4H,m), 7.1–7.3 (1H,m), 7.55–7.95 (2H,m), 8.45 (1H,d)

EXAMPLE 15

Pentyl 2-chloro-5-[[(5,6-dihydro-2-methyl-1,4-oxathiin-3-yl)carbonyl]amino]benzoate (Compound 15)

Thionyl chloride (3.9 g, 0.033 mole) was added to a stirred mixture of 5,6-dihydro-2-methyl-1,4-oxathiin-3-carboxylic acid (5.2 g, 0.032 mole) and methylene chloride (100 ml). The mixture was stirred overnight at room temperature, then evaporated under reduced pressure. The residue, crude 5,6-dihydro-2-methyl-1,4-oxathiin-3-carbonyl chloride, was dissolved in methylene chloride (100 ml), and the ice-chilled solution treated dropwise with a solution of pentyl 5-amino-2-chlorobenzoate (7.9 g, 0.033 mole) and triethylamine (3.3 g, 0.033 mole) in methylene chloride (100 ml). The reaction mixture was stirred at room temperature for 4 hours, then worked up by washing in sequence with water, dilute hydrochloric acid, water, 2% sodium hydroxide and water. Evaporation of the solvent left an oil, which solidified very slowly. After recrystallization from ethanol (30 ml) the product 5.9 g, 47% yield) melted at 65°–68° C. A second recrystallization raised the melting point to 70°–71° C.

Analysis: Calc.: C 56.32, H 5.78, N 3.65, Found: C 56.29, H 5.66, N 3.67

NMR: (CDCl$_3$) 0.7–1.9 (9H,m) 2.3 (3H,s), 3.0 (2H,m) 4.15–4.55 (4H,m), 7.15–8.1 (4H,m)

EXAMPLE 16

1-Methylethyl 2-chloro-5-[[(2,4,5-trimethyl-3-furanyl)carbonyl]amino]benzoate (Compound 16)

2,4,5-Trimethyl-3-furancarboxylic acid was prepared by the method of Hanson et al., J. Chem Soc. (1965), 5984.

2,4,5-Trimethyl-3-furancarbonyl chloride was prepared by refluxing 2,4,5-trimethyl-3-furancarboxylic acid (20.0 g) with thionyl chloride (20 ml) in toluene (75 ml) for 3 hours. The toluene and excess thionyl chloride were removed on a rotary evaporator and the residue distilled (b.p. 95°–97° C. at ca. 12 mm).

A solution of 2,4,5-trimethyl-3-furancarbonyl chloride (7.8 g, 0.045 mole) in toluene (25 ml) was added to 1-methylethyl 5-amino-2-chlorobenzoate (10.6 g, 0.050 mole) and triethylamine (6 g) in toluene (25 ml). The mixture was warmed to 60° C. for about 1 hour, then washed in sequence with dilute hydrochloric acid, water, aqueous 5% sodium bicarbonate and water. The solution was dried with magnesium sulfate, filtered and evaporated. The residue was crystallized from toluene/petroleum ether to give 6.7 g of a pale yellow solid, m.p. 83°–85° C.

Analysis: Calc.: C 61.89, H 5.73, N 4.01, Found: C 61.78, H 5.83, N 4.10

NMR: (DMSO-d6): 1.35 (6H,d), 1.98 (3H,s), 2.20 (3H,s), 2.42 (3H,s), 5.2 (1H,m), 7.4–8.2 (3H,m), 10.1 (1H,s)

EXAMPLE 17

1-Methyethyl 2-chloro-5-[(3-methyl-2-furanyl)carbonyl]amino]benzoate (Compound 17)

3-Methyl-2-furancarboxylic acid (41 g, m.p. 136°–138° C.) was prepared by refluxing methyl 3-methyl-2-furancarboxylate 54g, (Organic Synthesis, Coll. Vol. IV, p. 649), sodium hydroxide (20 g), water (100 ml) and ethanol (100 ml), then cooling and acidifying with concentrated hydrochloric acid.

3-Methyl-2-furancarbonyl chloride was prepared by refluxing 3-methyl-2-furancarboxylic acid (20.0 g) with thionyl chloride (25 ml) in toluene (75 ml) for 3 hours. After removal of the solvent, the acid chloride was distilled (b.p. 74°–76° C. at ca. 12 mm).

A solution of 3-methyl-2-furancarbonyl chloride (9.5 g, 0.066 mole) in toluene (20 ml) was added to 1-methylethyl 5-amino-2-chlorobenzoate (14 g, 0.066 mole) and triethylamine (10 g) in toluene (20 ml). After about three hours at ambient temperature, the mixture was washed with dilute hydrochloric acid, water, aqueous 5% sodium bicarbonate and finally water. With cooling, the product (m.p. 99°–100° C., 10 g, 47% yield) was crystallized from toluene.

Analysis: Calc.: C 59.81, H 4.98, N 4.36, Found: C 59.11, H 5.00, N 4.02

NMR: (DMSO-d6): 1.35 (6H,d), 2.37 (3H,s),5.2 (1H,m), 6.6 (1H,d), 7.44–8.29 (4H,m), 10.35 (1H,s)

EXAMPLE 18

1-Methylethyl 5-(benzoylamino)-2-chloro-4-fluorobenzoate (Compound 18)

A solution of benzoyl chloride (2.94 g, 0.021 mole) and 1-methylethyl 5-amino-2-chloro-4-fluorobenzoate (4.62 g, 0.020 mole) in methyl ethyl ketone (50 ml) was stirred at room temperature for 3 days. Evaporation of the solvent and crystallization of the solid residue from ethyl ether gave colorless needles, m.p. 117°–119° C. (6 g, 90% yield).

Analysis: Calc.: C 60.81, H 4.50, N 4.17, Found: C 60.89, H 4.72, N 4.08

NMR: (CDCl3) : 1.37 (6H,d), 5.25 (1H,m),7.20 (1H,d), 7.4–7.6 (3H,m), 7.75–8.0 (2H,m),8.15 (1H,bs), 8.83 (1H,d)

EXAMPLE 19

1-Methylethyl 2-chloro-5-[(2-methoxybenzoyl)amino]benzoate (Compound 19)

2-Methoxybenzoyl chloride (8.8 g, 0.05 mole) was added at room temperature under a dry nitrogen atmosphere to a stirred mixture of 1-methylethyl 5-amino-2-chlorobenzoate (10.7 g, 0.05 mole), triethylamine (5.6 g, 0.055 mole) and 4-(N,N,-dimethylamino)pyridine (catalyst, 0.2 g) dissolved in dry p-dioxane (100 ml . A solid Precipitate formed. Following the initial exothermic reaction (temperature increased to about 45° C.), the reaction mixture was stirred under nitrogen at room temperature for 20 hours. Next, the reaction mixture was added to water (500 ml), resulting in the precipitation of a solid product, which was collected by vacuum filtration, washed with water (500 ml), and dried to yield 16.2 g of the title compound, m.p. 94°–96° C.

NMR: (CDCl3) : 1.40 (6H,d) 4.05 (3H,s)5.28 (1H,m), 7.02 (1H,d), 7.11 (1H,m), 7.38 (1H,d), 7.49 (1H,m), 7.87 (1H,m), 7.95 (1H,d), 8.25 (1H,m), 9.86 (1H,s)

EXAMPLE 20

2,3,4,5-Tetrabromo-6-[[[4-chloro-2-fluoro-5-(1-methylethoxycarbonyl)phenyl]amino]carbonyl]benzoic acid (Compound 20)

Tetrabromophthalic anhydride (6.67 g, 0.014 mole) and 1-methylethyl 5-amino-2-chloro-4-fluorobenzoate (3.33 g, 0.014 mole) were heated to reflux with stirring in about 150 ml of toluene, then left overnight at room temperature. Filtration of the reaction mixture gave the title compound, m.p. 160°–165° C. (decomp.).

Analysis: Calc.: C 31.09, H 1.60, N 2.01, Found: C 31.27, H 1.57, N 2.12

NMR (DMSO-d6): 1.35 (6H,d), 5.2 (1H,m), 7.7 (1H,d), 8.45 (1H,d), 9.9 (1H,bs), 10.9 (1H,s)

EXAMPLE 21

2,3,4,5-Tetrabromo-6-[[[4-chloro-3-(1-methylethoxycarbonyl)phenyl]amino]carbonyl]benzoic acid (Compound 21)

Tetrabromophthalic anhydride (7.03 g, 0.015 mole), 1-methylethyl 5-amino-2-chlorobenzoate (3.24 g, 0.015 mole) and toluene (about 150 ml) were heated almost to reflux over 30 minutes. The reaction mixture was cooled and filtered to give the title compound, m.p. 169°–171° C. (decomp.) (8.92 g, 87% yield).

Analysis: Calc.: C 31.92, H 1.79, N 2.07, Found: C 33.00, H 2.00, N 2.12

NMR: (DMSO-d6): 1.35 (6H,d), 5.2 (1H,m) 7.4–8.2 (3H,m), 11.0 (1H,s), 12.0 (1H,bs)

EXAMPLE 22

2,3,4,5-Tetrachloro-6-[[[4-chloro-3-(1-methylethoxycarbonyl)phenyl]amino]carbonyl]benzoic acid (Compound 22)

A mixture of tetrachlorophthalic anhydride (2.97 g, 0.010 mole), 1-methylethyl 5-amino-2-chlorobenzoate (2.22 g, 0.010 mole) and toluene (100 ml) was heated slowly to reflux with stirring, then left overnight at room temperature. Filtration of the reaction mixture gave the title compound, m.p. 178°–179° C. (3.45 g, 70% yield).

Analysis: Calc.: C 43.28, H 2.42, N 2.80, Found: C 42 99, H 2.31, N 2.91

NMR: (DMSO-d6): 1.35 (6H,d), 5.2 (1H,m) 7.4–8.2 (3H,m), 11.2 (1H,s), 11.5 (1H,bs)

EXAMPLE 23

1-Methylethyl 2-chloro-5-[(2-methylbenzoyl)amino]benzoate (Compound 23)

A solution of 1-methylethyl 5-amino-2-chlorobenzoate (5.3 g, 0.025 mole) and triethylamine (3 g, 0.030 mole) in methylene chloride (50 ml) was added dropwise over 1 hour to an ice-cooled solution of o-toluyl chloride (4 g, 0.026 mole) in methylene chloride (50 ml). The mixture was then stirred at room temperature for 2 hours and worked up by sequential washing with water, dilute hydrochloric acid, water, 2% aqueous sodium hydroxide and water. The residue from evaporation of the methylene chloride was recrystallized from isopropyl alcohol (50 ml) to give the title compound, m.p. 137°-138° C. (4 g, 49% yield).

Analysis: Calc.: C 65.16, H 5.47, N 4.22, Found: C 64.75, H 5.01, N 3.95

NMR: (CDCl$_3$) : 1.4 (6H,d), 2.5 (3H,s), 5.25 (1H,m), 7.2-7.55 (5H,m), 7.7-8.0 (3H,m)

EXAMPLE 24

Propyl 2-chloro-5-[(2-methylbenzoyl)amino]benzoate (Compound 24)

A solution of propyl 5-amino-2-chlorobenzoate (10.7 g, 0.050 mole) and triethylamine (6 g, 0.059 mole) in methylene chloride (50 ml) was added dropwise over 1 hour to an ice-cooled solution of o-toluoyl chloride (7.8 g, 0.50 mole) in methylene chloride (50 ml). The mixture was then stirred at room temperature for 3 hours and worked up by washing sequentially with water, dilute hydrochloric acid, water, 2% aqueous sodium hydroxide and water. The residue from evaporation of the methylene chloride was recrystallized from ethanol (100 ml) to give the title compound, m.p. 103°-105° C. (7.5 g, 45% yield).

Analysis: Calc.: C 65.16, H 5.47, N 4.22, Found: C 64.79, H 4.91, N 4.11

NMR: (CDCl$_3$) : 1.0 3H,t), 1.7 (2H,m),2.5 (3H,s), 4.25 (2H,t), 7.2-7.55 (5H,m), 7.65-8.0 (3H,m)

EXAMPLE 25

N-(4-Chlorophenyl)-5,6-dihydro-3-methyl-1,4-dithiin-2-carboxamide (Compound 26)

2-Chloro-N-(4-chlorophenyl)-3-oxobutanamide (24.7 g, 0.1 mole), 1,2-ethanedithiol (9.4 g, 0.1 mole) and a small amount of p-toluenesulfonic acid were heated under reflux in benzene (150 ml), using a Dean-Stark trap to remove water (1.9 ml collected). The reaction mixture was filtered, treated with triethylamine (8 ml), and refluxed for a further 30 minutes. The mixture was then washed with water, dilute hydrochloric acid, and water. Evaporation of the benzene gave a white solid, which was recrystallized from absolute ethanol. The product melted at 115°-117° C. (24 g, 84% yield).

Analysis: Calc.: C 50.43, H 4.20, Found: C 50.18, H 4.15

EXAMPLE 26

1-Methylethyl 2-chloro-5-[[(5,6-dihydro-3-methyl-1,4-dithiin-2-yl)carbonyl]amino]benzoate (Compound 27)

5,6-Dihydro-3-methyl-1,4-dithiin-2-carboxylic acid was prepared by the method of U.S. Pat. No. 4,004,018, col. 11, lines 24-38.

Thionyl chloride (6.5 g, 0.055 mole) was added slowly to a stirred solution of 5,6-dihydro-3-methyl-1, 4-dithiin-2-carboxylic acid (3 g, 0.017 mole) in toluene (15 ml) at room temperature. The mixture was heated under reflux for 4 hours. The excess toluene and thionyl chloride were removed in a rotary evaporator, yielding the crude acid chloride. 1-Methylethyl 5-amino-2-chlorobenzoate (3 g, 0.014 mole) in pyridine (20 ml) was added slowly to a stirred solution of the crude acid chloride (3 g) in methylene chloride (20 ml) at 20° C. The mixture was stirred for 24 hours, poured onto ice and concentrated hydrochloric acid, washed twice with water, dried with magnesium sulfate, and the methylene chloride evaporated. Recrystallization from 95% ethanol yielded the title compound, m.p. 122°-124° C. (3 g, 57% yield).

Analysis: Calc.: C 51.6, H 4.88, N 3.77, Found: C 51.43, H 4.70, N 3.72

NMR: (DMSO-d6) : 1.4 (6H,d), 2.1 (3H,s), 3.3 (4H,bs), 5.2 (1H,m), 7.4-8.25 (3H,m)

EXAMPLE 27

1-Methylethyl 2-chloro-5-(5,6-dihydro-3-methyl-1,4-dioxin-2-yl)carbonyl]amino]benzoate (Compound 28)

Trifluoroacetic anhydride (100 g, 0.5 mole) was added dropwise to an ice-cooled solution of 2,3-dihydro-5-methyl-1,4-dioxin (30 g, 0.30 mole) in methylene chloride (50 ml) and pyridine (40 g, 0.50 mole). The mixture was stirred overnight and then evaporated under reduced pressure. To the residue was added ether (150 ml) and 10% sodium carbonate solution. The ether phase was separated, washed with dilute hydrochloric acid and water, dried over anhydrous sodium sulfate, filtered and evaporated to leave an oil, 1-(5,6-dihydro-3-methyl-1,4-dioxin-2-yl)-2,2,2-trifluoroethanone (12 g, 20% yield).

A mixture of 1-(5,6-dihydro-3-methyl-1,4-dioxin-2-yl)-2,2,2-trifluoroethanone (12 g, 0.06 mole) and powdered potassium hydroxide (6 g, 0.1 mole) was refluxed in toluene (200 ml) for 7 hours. The mixture was cooled, acidified with 6N hydrochloric acid, and the solid precipitate, crude 5,6-dihydro-3-methyl-1,4-dioxin-2-carboxylic acid (6 g, 60% yield) collected.

A mixture of thionyl chloride (1.3 g, 0.011 mole) and 5,6-dihydro-3-methyl-1,4-dioxin-2-carboxylic acid (0.57 g, 0.004 mole) was refluxed on a steam bath for 3 hours and the excess thionyl chloride was evaporated at atmospheric pressure. The resulting liquid was added dropwise to a stirred solution of 1-methylethyl 5-amino-2-chlorobenzoate (1.6 g, 0.008 mole) in diethyl ether (30 ml), cooled in an ice-water bath. The mixture was worked up by diluting with diethyl ether (120 ml), washing with dilute hydrochloric acid (50 ml), and then with water (50 ml). The diethyl ether solution was dried over anhydrous sodium sulfate, filtered and evaporated under reduced pressure, leaving a solid residue. The crude product was washed with isopropyl alcohol (30 ml), leaving a brown solid, m.p. 103°-105° C. (1.2 g, 95.8% yield).

NMR: (CDCl$_3$) : 1.4 (6H,d), 2.3 (3H,s), 4.2 (4H,s), 5.3 (1H,m), 7.3-8.0 (3H,m), 8.3 (1H,bs)

EXAMPLE 28

1-Methylethyl 2-chloro-5-[[1-methylethoxycarbonyl]amino]benzoate (Compound 29)

Hydrogen chloride was bubbled into a solution of 1-methylethyl 5-amino-2-chlorobenzoate (35 g, 0.16 mole)in dry diethyl ether (500 ml). The resulting precipitate was filtered off, washed with ether and dried overnight in a vacuum desiccator. It was then suspended in ethyl acetate and excess phosgene bubbled into the stirred, refluxing mixture over 45 minutes. Part of the ethyl acetate was distilled off to remove excess phosgene, then the rest of the solvent was removed under reduced pressure and the residual 1-methylethyl 2-chloro-5-isocyanatobenzoate distilled at 114° C./0.1 mm 28 g, 71% yield).

NMR (CDCl₃): 1.39 (6H,d), 5.26 (1H,m), 6.98–7.52 (3H,m)

1-Methylethyl 2-chloro-5-isocyanatobenzoate (3 g, 0.013 mole) in tetrahydrofuran (5 ml) was added to isopropyl alcohol (5 ml) in tetrahydrofuran (5 ml). A few drops of triethylamine were added and the reaction mixture left at ambient temperature overnight. Removal of the solvent and crystallization from isopropyl alcohol gave the title compound, m.p. 108°–109° C. (2.7 g).

Analysis: Cal. C 56.18, H 6.02, N 4.68, Found: C 55.66, H 5.93, N 4.51

NMR: (DMSO-d6): 1.27 (6H,d), 1.35 (6H,d), 4.7–5.38 (2H,m), 7.38–8.0 (3H,m), 9.9 (1H,s)

EXAMPLE 29

1-Methylethyl 2-chloro-5-[(2,2-dimethyl-1-oxopropyl)amino]-4-fluorobenzoate (Compound 30)

A solution of trimethylacetyl chloride (2.53 g, 0.021 mole) and 1-methylethyl 5-amino-2-chloro-4-fluorobenzoate (4.62 g, 0.020 mole) in methyl ethyl ketone was stirred at room temperature for 16 hours and then refluxed for 2 hours. The solvent was removed and the residue triturated with diethyl ether to give a tan solid, m.p. 81°–83° C. (5.0 g, 79% yield).

Analysis: Calc.: C 57.06, H 6.06, N 4.44, Found: C 56.83, H 6.08, N 4.38

NMR: (CDCl₃) : 1.33 (9H,s), 1.38 (6H,d), (5.25 (1H,m), 5.25 (1H,m), 7.18 (1H,d), 7.60 (1H,bs), 8.77 (1H,d)

EXAMPLE 30

Preparation of 1-methylethyl 2-chloro-5-[(2-methyl-3-furanyl)thioxomethyl]amino benzoate (Compound 59)

A mixture of 3.5g 1-methylethyl 2-chloro-5-[[(2-methyl-3-furanyl)carbonyl]amino]benzoate, 4.0g Lawesson's reagent was refluxed in toluene for seven hours. The solvent was removed and the residue eluted from a silica gel column with a 40:60 mixture of ethyl acetate: hexane. An oil was obtained from the first fraction which on crystallization from toluene/petroleum ether gave a yellow solid (0.9g) m.p. 83°–85° C.

Analysis: Calc.: C 56.97, H 4.75, N 4.15, Found: C 56.86, H 4.69, N 3.83

NMR spectrum (CDCl₃) gave ppm values 1.30 (3H,s) 1.40 (3H,s) 2.65(3H,s) 5.0–5.5 (1H,quartet) 6.55–6.62 (1H,d) 7.15–8.0(4H,m) 8.7–9.05(1H,s)

EXAMPLE 31

1-Methylethyl 2-chloro-5-[(2,5-diethyl-3-furanyl)thioxomethyl)amino]benzoate (Compound 60) was prepared in a manner similar to Example 30.

NMR spectrum (CDCl₃) gave ppm values 1.40 (3H,s) 1.50(3H,s) 2.69(3H,s) 5.0–5.6 (1H,quartet) 6.25 (1H,s) 7.38–8.1 (2H,m) 8.78–9.05 (1H,s)

EXAMPLE 32

1-Methylethyl 2-chloro-5-[(2,4,5-trimethyl 3-furanyl)thioxomethyl]amino]benzoate (Compound 58) was prepared in a manner similar to Example 30.

Analysis: Calc.: C:59.18, H:5.48, N:3.84, Found: C:58.94, H:5.49, N:4.40

EXAMPLE 33

Benzoic acid, 2-chloro-5-[(phenylthioxomethyl)amino]ethyl ester (Compound 62)

A solution of benzoic acid, 5-(benzoylamino)-2-chloro-, ethyl ester (3.0g, 10m moles) and 4.12 (10m moles) of Lawesson's reagent in 100 ml of dry toluene was stirred and refluxed for nine hours. The solution was concentrated then purified through a short column of silica gel (70–230 mesh) using ethyl ether: hexane (1:1) as eluent. A bright amber solid was obtained m.p. 125°–127° C., yield 2.6g (80%) Analysis: Calc: C 60.9, H 4.41, N 4.38, Found: C 59.88, H 4.43, N 4.28

NMR: (CDCl₃) 1.36(3H,t), 4.34(2H,m), 7.3–8.1 (8H,m), 9.23(1H,bs)

EXAMPLE 34

Benzoic acid, 2-chloro-5-(phenylthioxomethyl) amino-, 1-methylethyl ester (Compound 61)

A solution of benzoic acid, 5-(benzoylamino)-2-chloro-, 1-methylethyl ester (3.2g, 10mmoles) and 4.04g of Lawesson's reagent in 150 ml of dry toluene was stirred and refluxed for 40 hours. The solution was concentrated then purified through a short column of aluminum oxide using ethyl ether: hexane (1.3) as eluents. The amber solution was concentrated to give bright amber solid m.p. 93°–94° C. yield, 1.5g (44.6%).

NMR δ(CDCl₃) 1.30–1.40(d,6H), 5.23(m,1H) 7.2–8.1(m,8H) 9.30 (bs,1H)

Analysis: Calc.: C 61.16, H 4.83, N 4.20, Found: C 61.24, H 4.84, N 4.52

EXAMPLE 35

Benzoic Acid, 2-chloro-5-(3-methyl-1-thioxo-2-butenyl)amino-, 1-methylethyl ester (Compound 67)

A solution of benzoic acid, 2-chloro-(3-methyl-1-oxo-2-butenyl)amino-, 1-methylethyl ester (3,7g, 12.5 mmoles) and Lawesson's reagent (5.1 g, 12.5 mmoles) in 100 ml of dry toluene was stirred and refluxed for 40 hours. The final solution was concentrated then purified through a short column of silica gel (70–230 mesh) using ethyl ether as eluent. An orange oil (5 g) was obtained. This crude product was purified further with a column of aluminum oxide using ethyl ether: hexane (1:3) as eluent. A light amber solution was obtained which was concentrated to give a light amber solid m.p. 85°–86° C., yield 2.8 g, (72%)

Analysis: Calc.: C 57.78, H5.82, N 4.49, Found: C 57.05, H5.54, N 5.70

NMR: δ(CDCl₃) 1.33, 1.40 (d,6H); 1.83–2.03 (dd,6H) 5.26(m,1H), 6.13(unresolved m,1H), 7.23–7.8 (m,3H) 7.9 (bs,1H)

EXAMPLE 36

1-Methylethyl 2-chloro-5-[[(1-methylethoxy)thioxomethyl]amino]benzoate (Compound 32)

This is the preparation of compound 32 using 1,3-dicyclohexylcarbodiimide. A mixture of 2-chloro-5-[[(1-methylethoxy)thioxomethyl]amino]benzoic acid (2 g, 0.007 mol), isopropyl alcohol (1.3 g, 0.02 mol), 4-dimethylaminopyridine (0.85 g, 0.007 mol) in 25 ml methylene chloride was stirred in an ice bath and 1,3-dicyclohexylcarbodiimide (1.7 g 0.008 mol) added. The mixture was allowed to come to ambient temperature and stirred overnight. The precipitated solid was filtered off and the filtrate washed with dilute hydrochloric acid and aqueous 5% sodium bicarbonate. After drying over magnesium sulfate, filtering and removing the methylene chloride, the product was crystallized from toluene/petroleum ether. Yield 1.2 g m.p. 89° C. A mixed m.p. with authentic compound 32 also gave m.p. 89°-90° C. The N.M.R. spectrum was identical with that of authentic compound 32.

Analysis: Calc.: C 53.33, H5.71, N 4.44, Found: C 53.44, H5.62, N 4.42

NMR: $\delta(CDCl_3)$ 1.35(6H,d), 1.45 (6H,d); 5.0-5.8 (2H,m) 7.28-7.80(3H,m), 8.43(1H,s)

IN VITRO SCREENING RESULTS

The compounds of Examples were tested for anti-AIDS activity by subjecting them to standard National Cancer Institute ("NCI") in vitro screening procedures. In carrying out each test, two blanks were run. In the first blank, HIV and a culture of a standard human cell line were incubated together to measure the infectivity of the virus. The viability of the cells was measured after holding for six or seven days. In an "effective" test, most cells were infected before the holding period was complete.

In the second blank, the cell line culture and the compound being tested (but not virus) were incubated together to measure the toxicity of the drug to the cell-line. The viability of the cells was measured as a function of concentration of the compound, after holding for seven days. Typically, the cells survive at low compound concentrations, but at some higher concentration, toxicity of the compound is manifested and the cells die. The concentration of the test compound that results in 50% inhibition of cell growth is defined as the IC50.

Finally, the protective effects of the test compounds were measured. Each cell culture and test compound were incubated with the virus and the viability of the cells was measured as a function of compound concentration after holding for six or seven days. If the compound is active in protecting the cells against the virus, there is typically low cell viability until an effective concentration of the test compound is reached. At this point, cell viability increases steadily toward 100% unless the toxic effect of the compound (as measured in the second blank) takes effect. The concentration of the test compound that results in 50% "control," i.e., a 50% reduction of the viral cytopathic effect, is defined as the EC 50. The therapeutic index TI50 is calculated as IC50/EC50.

Values of test compound concentrations required for between 20 and 50% reduction of the viral cytopathic effect can also be determined. Such compounds are classified as moderately active. Compounds with less than 20% control are considered inactive.

The compounds were tested to determine their reduction of HIV cytopathic effect on the human cell lines CEM and MT2. Tests were done by innoculating these cell lines either with free HIV (V) or with a virus previously cultured with host cells (C). Thus, in Table III the designation CEMV means CEM line cells innoculated with free virus and MT2C means MT2 cells innoculated with cultured viral infected MT2 cells. In some cases the compound was also tested on a cell line together with a sub-effective amount of the known HIV viricide AZT. This is done to test possible synergistic effects. Such a test on the CEM line is denoted CEMZ.

The Test Procedure

1) T4 lymphocytes (CEM cell line) are exposed to HIV at a virus to cell ratio of approximately 0.05 and plated along with non-infected control cells in 96-well microtiter plates.
2) Each candidate agent is dissolved in dimethyl sulfoxide (unless otherwise indicated), then diluted 1:200 in cell culture medium. Further dilutions (five-fold) are prepared before adding to an equal volume of medium containing either infected or noninfected cells.
3) Cultures are incubated at 37° C. in a 5% carbon dioxide atmosphere for seven days (if six days the CEMV test is identified as CEM-6).

The aforementioned identifiers are used when a batch was prepared and samples inserted into the wells. In procedures calling for the addition of the drug (or no drug) and the CEM uninfected cells to each well, followed by the subsequent addition of the HIV virus, the protocol is designated as CEM-IW.

4) The tetrazolium salt, XTT, is added to all wells, and cultures are incubated to allow formazan color development by viable cells.
5) Individual wells are analyzed spectrophotometrically to quantity formazan production, and in addition are viewed microscopically for detection of viable cells and confirmation of protective activity.
6) Drug-treated virus-infected cells are compared with drug-treated non-infected cells and with other appropriate controls (untreated infected and untreated non-infected cells, drug-containing wells without cells, etc.) on the same plate.
7) A determination of activity is made.

Screening Data for Test Compounds Exhibiting Inhibition of HIV

The preceding protocol was carried out with the compounds of the examples all of which showed some significant activity in at least one of the tests. All test results (molar) for all compounds exhibiting greater than 50% inhibition of the virus in any of the tests are shown in Table II as EC50's. Also shown are results for compounds exhibiting moderate activity (MA), that is, inhibition between approximately 20 and 50%. Tests in which a compound was inactive (less than 20% inhibition) are denoted as I.

TABLE II

| Activity of Anti-HIV Compounds (EC50) Concentration (moles/liter $\times 10^{-6}$) | | | | | |
|---|---|---|---|---|---|
| COMPOUND | MT2C | MT2V | CEMC | CEMV | CEMZ |
| 1 | 1.2 | 2.6 | 1.2 | 0.2 | |
|  | 0.9 |  | 0.7 | 0.3 | |
|  | 4.2 |  | 39.2 | 8.8 | |
|  | 0.009 |  | 0.6 | 11.8 | |
|  | 0.4 |  | 0.4 | 1.0 | |
|  |  |  |  | 0.05 | |
| 2 | 3.2 | 14.4 | 3.5 | 1.3 | 1.8 |
|  |  |  |  | 1.5 | |
|  |  |  |  | 0.9 | |
|  |  |  |  | 4.3 | |
|  |  |  |  | 6.3 | |
|  |  |  |  | 1.3 | |
|  |  |  |  | 0.2 | |
| 3 |  |  |  | 6.1 | |
|  |  |  |  | 4.6 | |
|  |  |  |  | 1.4 | |
|  |  |  |  | 1.9 | |
| 4 |  |  |  | 0.4 | |
|  |  |  |  | 0.3 | |

TABLE II-continued
Activity of Anti-HIV Compounds (EC50)
Concentration (moles/liter × 10⁻⁶)

| COMPOUND | MT2C | MT2V | CEMC | CEM-6 | CEMZ |
|---|---|---|---|---|---|
| 5 | | | | 0.2 | |
| | | | | .07 | |
| | | | | .06 | |
| 6 | | | | 0.1 | |
| 7 | | | | 0.84 | |
| | | | | 0.70 | |
| 8 | MA | | | | |
| | MA | | | | |
| 9 | | MA | | | |
| | | MA | | | |
| | | MA | | | |
| 10 | | | | 3.0 | |
| | | | | 2.9 | |
| 11 | | | | 0.15 | |
| | | | | 0.07 | |
| | | | | (CEM-6) | |
| | | | | 0.258 | |
| | | | | 0.280 | |
| | | | | 0.172 | |
| | | | | 0.143 | |
| | | | | 0.236 | |
| | | | | 0.076 | |
| | | | | 0.067 | |
| 12 | | | | 1.2 | |
| | | | | 3.3 | |
| 13 | | | | 15.2 | |
| | | | | 13.2 | |
| 14 | | | | 7.6 | |
| | | | | 5.2 | |
| 15 | | | | 0.82 | |
| | | | | 0.61 | |
| 16 | | | | 3.0 | 0.9 |
| | | | | 9.6 | |
| | | | | 8.4 | |
| | | | | 0.4 | |
| | | | | 1.6 | |
| | | | | 1.2 | |
| 17 | | | | 3.3 | 7.9 |
| 18 | | | | 8.1 | |
| | | | | 7.8 | |
| | | | | 2.5 | |
| | | | | 6.7 | |
| 19 | | | | 3.1 | |
| | | | | 2.3 | |
| | | | | 0.4 | |
| | | | | 0.8 | |
| 20 | | | | 69.5 | |
| | | | | 58.7 | |
| | | | | 69.4 | |
| | | | | 54.5 | |
| 21 | | | | 58.2 | |
| | | | | 36.2 | |
| 22 | | | | 88.6 | |
| | | | | 75.4 | |
| | | | | 32.7 | |
| 23 | | | | 5.8 | 1.1 |
| | | | | 5.6 | |
| 24 | | | | 11.1 | 12.0 |
| | | | | 0.9 | |
| 25 | | | | 466 | 34.4 |
| | | | | 228 | 39.4 |
| 26 | MA | 35.5 | | MA | |
| | MA | | | I | |
| 27 | | | | 1.38 | |
| | | | | 0.81 | |
| 28 | | | | 11.6 | |
| | | | | 28.5 | |
| | | | | 7.7 | |
| 29 | | | | 5.6 | |
| | | | | 11.9 | |
| | | | | 7.8 | |
| | | | | 1.4 | |
| | | | | 1.5 | |
| 30 | | | | I | |
| | | | | I | |
| | | | | MA | |
| | | | | MA | |
| | | | | 42.7 | |
| 31* | | | | 2.84 | |
| | | | | 2.14 | |
| | | | | 5.43 | |
| | | | | 5.85 | |
| 32 | | | | 0.035 | |
| | | | | 0.059 | |
| | | | | 0.030 | |
| | | | | (*CEM-IW) | |
| 33* | | | | 0.66 | |
| | | | | 0.68 | |
| | | | | 0.68 | |
| | | | | 0.73 | |

| COMPOUND | MT2C | MT2V | CEMC | CEM-6 | CEMZ |
|---|---|---|---|---|---|
| | | | | CEM-6 | |
| 34 | | | | 0.13 | |
| | | | | 0.073 | |
| | | | | .46 | |
| 35* | | | | 0.24 | |
| | | | | 0.24 | |
| | | | | 0.18 | |
| | | | | 0.20 | |
| 36* | | | | 1.04 | |
| | | | | 1.38 | |
| | | | | 1.32 | |
| | | | | 0.89 | |
| 37* | | | | 0.32 | |
| | | | | 0.32 | |
| | | | | 0.32 | |
| | | | | 0.20 | |
| 39* | | | | 1.75 | |
| | | | | 1.46 | |
| | | | | 1.09 | |
| | | | | 1.47 | |
| 43* | | | | MA | |
| 44 | | | | 0.76 | |
| | | | | 1.34 | |
| 46 | | | | 0.21 | |
| | | | | 0.053 | |
| | | | | 0.053 | |
| 47* | | | | 0.45 | |
| | | | | 0.41 | |
| | | | | 1.33 | |
| | | | | 1.44 | |
| 48 | | | | MA | |
| 49 | | | | MA | |
| 50* | | | | 1.06 | |
| | | | | 1.78 | |
| | | | | 0.74 | |
| | | | | 0.83 | |
| 52* | | | | 2.44 | |
| | | | | 2.47 | |
| | | | | 1.94 | |
| 58* | | | | 0.87 | |
| | | | | 0.75 | |
| | | | | 1.06 | |
| | | | | 0.90 | |
| 59* | | | | 0.043 | |
| | | | | 0.037 | |
| 60* | | | | 0.15 | |
| | | | | 0.17 | |
| | | | | 0.11 | |
| | | | | 0.13 | |
| 61* | | | | 0.39 | |
| | | | | 0.62 | |
| | | | | 0.42 | |
| | | | | 0.45 | |
| 62* | | | | 0.398 | |
| | | | | 0.317 | |
| | | | | 0.267 | |
| | | | | 0.0622 | |
| 64* | | | | 0.0735 | |
| | | | | 0.0329 | |
| 65* | | | | 0.476 | |
| | | | | 0.404 | |
| | | | | 0.588 | |
| | | | | 0.509 | |
| 69 | | | | 0.34 | |
| | | | | 0.34 | |
| 70 | | | | 0.17 | |

TABLE II-continued

Activity of Anti-HIV Compounds (EC50)
Concentration (moles/liter × $10^{-6}$)

| Compound | Value |
|---|---|
|  | 0.21 |
|  | 0.23 |
| 71 | 0.99 |
|  | 1.83 |
|  | 1.62 |
| 72 | 0.54 |
|  | 0.59 |
|  | 0.34 |
| 73 | 0.41 |
|  | 0.58 |
| 74 | 38.9 |
| 75 | 1060 |
|  | 908 |
| 76 | MA |
| 77* | 5.06 |
|  | 3.12 |
|  | 15.1 |
|  | 16.4 |
| 78 | MA |
| 78* | MA |
| 79 | 3.3 |
|  | 3.1 |
|  | 1.4 |
|  | 4.5 |
|  | 3.3 |
|  | 3.3 |
| 80 | 3.6 |
|  | 6.7 |
|  | 2.3 |
|  | 2.5 |
|  | 2.3 |
| 81 | 0.42 |
| 82* | 2.67 |
|  | 2.56 |
|  | 2.15 |
|  | 2.88 |
| 83* | MA |
| 84 | MA |
| 85 | 0.82 |
|  | 1.02 |
|  | 0.42 |
| 86 | 1.74 |
|  | 1.36 |
| 87 | MA |
| 88 | 5.7 |
|  | 3.1 |
| 89 | 7.5 |
|  | 7.3 |
|  | 2.6 |
|  | 1.8 |
| 90 | MA |
| 91 | MA |
| 92 | MA |
| 93 | 1.36 |
|  | 2.77 |
| 94 | MA |
| 94* | MA |
| 98* | 0.89 |
|  | 0.73 |
|  | 0.35 |
|  | 0.51 |
| 99* | MA |
| 102* | MA |
| 103 | MA |
| 104 | MA |
| 105 | MA |
| 106 | 5.3 |
|  | 2.3 |
|  | 2.6 |
|  | 2.2 |
|  | 2.2 |
| 107 | MA |
| 108 | MA |
| 109 | MA |
| 112* | MA |
| 114* | MA |
| 117* | MA |
| 130* | MA |
| 131* | MA |
| 145* | 0.260 |
|  | 0.373 |
|  | 0.243 |
|  | 0.422 |
| 146* | 42.0 |
|  | 3.50 |
|  | 5.29 |
| 147* | 0.590 |
|  | 0.608 |
| 148* | MA |
| 149* | 0.0448 |
|  | 0.0901 |
|  | 0.0677 |
|  | 0.170 |
| 150* | 0.210 |
|  | 0.230 |
|  | 0.296 |
|  | 0.329 |
| 151* | 0.0954 |
|  | 0.0842 |
|  | 0.0777 |
|  | 0.0537 |
| 152* | 0.0717 |
|  | 0.0417 |
|  | 0.0368 |
|  | 0.0571 |
| 153* | 0.0719 |
|  | 0.0426 |
|  | 0.0530 |
|  | 0.0719 |
| 154* | 0.0443 |
| 155* | 0.0394 |
|  | 0.0607 |
|  | 0.0381 |
|  | 0.0301 |
| 156* | 0.486 |
|  | 0.632 |
|  | 1.19 |
|  | 1.04 |
| 157* | MA |
| 158* | 6.10 |
|  | 6.77 |
|  | 4.49 |
|  | 3.62 |
| 159* | 0.0589 |
|  | 0.0839 |
|  | 1.07 |
|  | 1.02 |

Asterisks indicate the CEM-IW protocol.

For compounds giving greater than 50% control (i.e., which have a true EC50), the EC50 is given for each test. Compounds giving between 20% and 50% control are listed as moderately active (MA) for each test.

Screening of the Compound of Example 3 With CEM Cell Line

The compound of Example 3, viz., methyl 2-chloro-5-[[(5,6-dihydro-2-methyl-1,4-oxathiin-3-yl)carbonyl]amino]benzoate, was tested against the H9/HTLV-IIIB (HIV-I) virus employing the CEM line of host cells and using free (HIV-I) virus employing the CEM line of host cells and using free virus innoculation (denoted CEM-V). The concentrations of the test compound that resulted in 50% inhibition of cell growth (IC50), the concentration of the compound that was effective in achieving 50% reduction in the viral cytopathic effect (EC50), and the therapeutic index I50) are shown in Table III below. All concentrations are expressed in moles per liter.

TABLE III

| INDEX | SUMMARY CONCENTRATION |
|---|---|

TABLE III-continued

| | |
|---|---|
| IC50 (Molar) | $1.01 \times 10^{-4}$ |
| EC50 (Molar) | $1.91 \times 10^{-6}$ |
| TI50 (IC/EC) | $5.31 \times 10^{+2}$ |

CONCLUSION
ACTIVE

| INFECTED CULTURE | | UNINFECTED CULTURE | |
|---|---|---|---|
| Dose (Molar) | Response (%) | Dose (Molar) | Response (%) |
| $5.47 \times 10^{-8}$ | 15.3 | $5.47 \times 10^{-8}$ | 86.8 |
| $1.72 \times 10^{-7}$ | 23.3 | $1.72 \times 10^{-7}$ | 86.8 |
| $5.46 \times 10^{-7}$ | 15.7 | $5.46 \times 10^{-7}$ | 84.0 |
| $5.45 \times 10^{-6}$ | 78.8 | $1.72 \times 10^{-6}$ | 84.6 |
| $1.72 \times 10^{-5}$ | 89.2 | $5.45 \times 10^{-6}$ | 107.9 |
| $5.44 \times 10^{-5}$ | 86.1 | $1.72 \times 10^{-5}$ | 95.7 |
| $1.72 \times 10^{-4}$ | 10.7 | $5.44 \times 10^{-5}$ | 97.0 |
| | | $1.72 \times 10^{-4}$ | 10.1 |

The same data are plotted in Figure I. The number of viable CEM test cells as a percentage of the number of cells in an uninfected, untreated CEM control culture is plotted against the concentration of the test compound in varying cultures of the CEM cell line.

The viral cytopathic effect in this experiment is indicated by a dotted reference line. This line shows the extent of destruction of cells by the virus in the absence of treatment and is used as a quality control parameter. Values of this parameter less than 50% are considered acceptable in the current protocol. This plot represents the first blank test.

The dashed line connecting the square symbols depicts the percentage of surviving uninfected cells treated with the sample relative to the same uninfected, untreated controls. This line expresses the in-vitro growth inhibitory properties of the sample and represents the second blank test. The plot thus shows toxicity of the test compound to the cell line, the uninfected treated culture being viable up to the concentration of the test compound that is toxic to the host cells.

The solid line connecting the square symbols depicts the percentage of surviving HIV-infected cells treated with the sample (at the indicated concentration) relative to the uninfected, untreated control. This line expresses the in vitro anti-HIV activity of the sample.

Up to point 5, low cell viability was obtained. Starting after point 5, an effective concentration of the test compound was obtained, and cell viability rapidly increased to point 6, above which the high concentration of the test compound poisoned the CEM cells.

It may be seen from Figure I that the compound of Example 3 began to show inhibition of the viral cytopathic effect (point 5) at a concentration of about $5.5 \times 10^{-7}$ molar and shows maximum effect at a concentration of about $1.7 \times 10^{-5}$ molar (point 6). The compound would thus be expected to be effective and safe to use between these two values. The compound of Example 3 was also tested in p24 and SFU tests to confirm activity against the HIV virus.

P24 is a specific antibody/antigen test that measures the amount of viral protein in the cell by linking with the virus's core protein. Unlike the Previous tests described above, which measured the survival of host cells, this test measures survival of the virus.

The SFU (Syncytia Forming Units) test indicates how extensively the virus has infected the host cell. Normally, protein in the HIV virus combines with a protein in the host cell. This protein is then expressed on the surface of the host cell, which causes that cell to fuse to another cell. Giant conglomerates are formed and can be easily counted.

Figure 2:
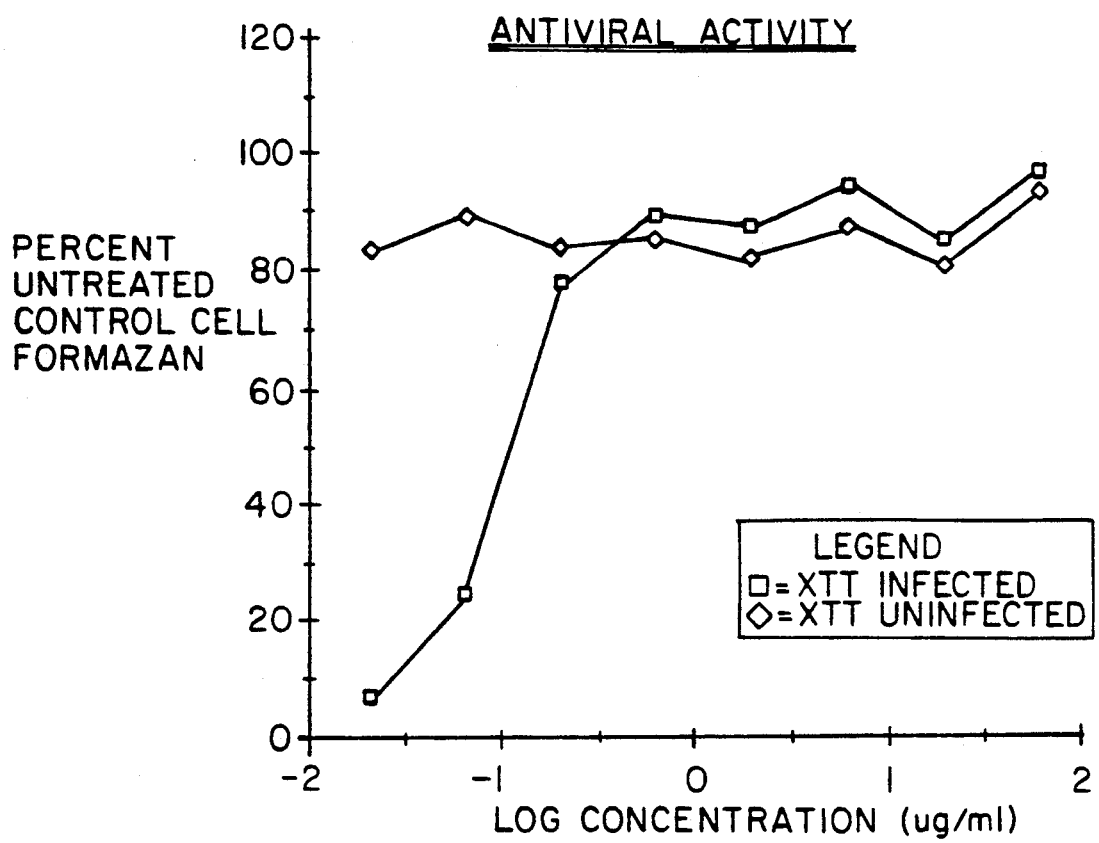
FIG. 2 is a graph showing antiviral activity of the compound of Example 3 versus concentration.
Figure 3:
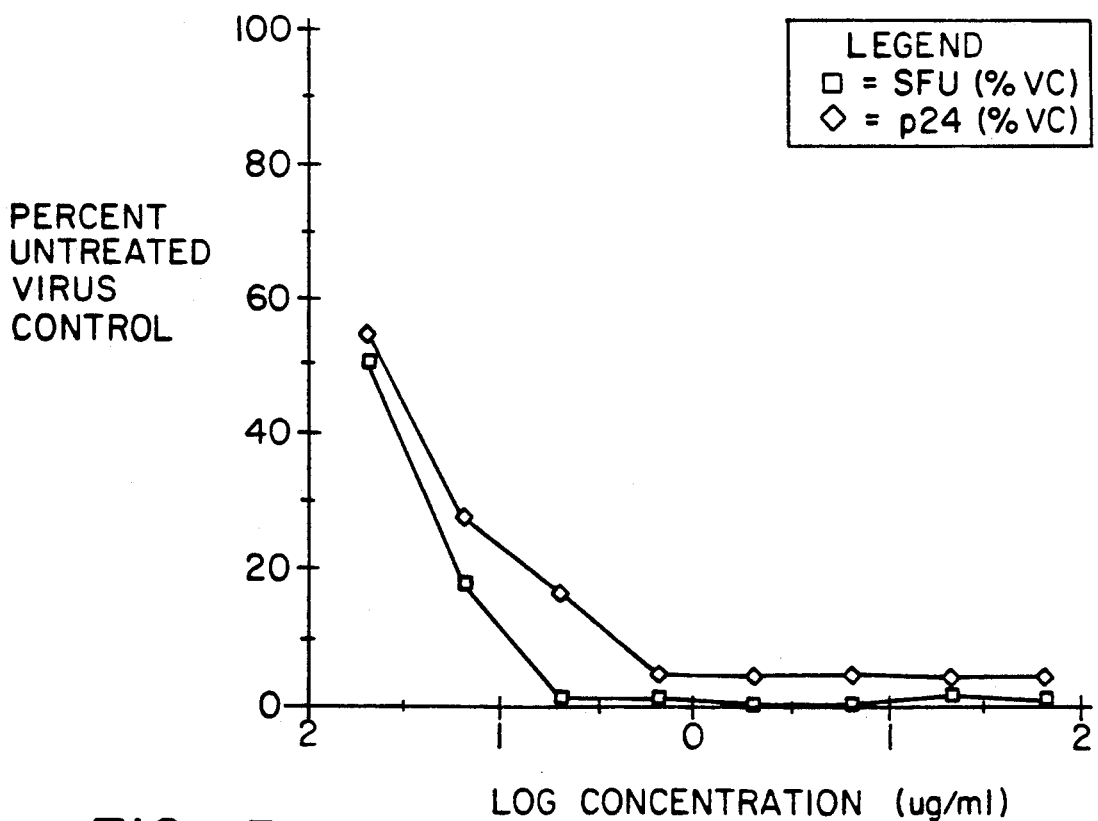
FIG. 3 is a graph showing effect on infectious virus and p24 production of the compound of Example 3 versus concentration.

The activity of the compounds of the invention was confirmed by these tests, as shown in FIGS. 2 and 3.

Initial studies on the toxicity of the compound of Example 1 were made on mice. These tests are summarized in Table IV below:

TABLE IV

| Dosage, mg/Kg per day for 5 days | Times Administered Per Day | Type of Test | Result, Toxicity |
|---|---|---|---|
| 10 | 2 | IV | No visible sign |
| 100 | 2 | IP | " |
| 750 | 1 | Oral | " |

In addition it has been found that the compound of Example 3 exhibits full HIV antiviral activity for up to eight hours after infection of the virus, and delays of up to twenty hours will still offer some protection. This is in contrast to AZT which is no longer effective after about four hours after infection.

The preceding is by way of example only and the scope of the invention is to be limited only by the scope of the appended claims.

We claim:

1. A compound having the formula:

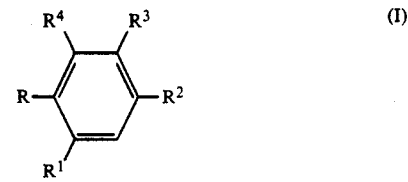

(I)

wherein:
$R^1$ is hydrogen, halogen, $C_1$–$C_4$ alkyl or $C_1$–$C_4$ alkoxy;

$R^2$ is hydrogen, halogen, $C_1$–$C_4$ alkyl, $C_1$–$C_4$ alkoxy, hydroxy, mono-, di- or tri-halomethyl, trifluoromethoxy, methylthio, nitro, cyano, acetoxy or dimethylamino;

$R^3$ is —$CO_2R^5$ wherein $R^5$ is an alkyl, $C_3$–$C_6$ alkenyl or alkynyl, a one to six haloalkyl, an alkoxyalkyl, an alkylthioalkyl, a carboxyalkyl, an alkylcarboxyalkyl, a $C_6$–$C_{12}$ arylcarboxyalkyl, an alkylaminoalkyl or dialkylaminoalkyl, a trialkylsilylalkyl, each of the aforementioned alkyl moieties having from one to eight carbon atoms; a phenyl, a naphthyl, a $C_1$–$C_6$ alkylphenyl, a $C_7$–$C_{12}$ arylalkyl or alkarylalkyl, a $C_3$–$C_8$ carbocyclyl, a $C_1$–$C_4$ alkyl $C_3$–$C_8$ carbocyclyl;

$R^4$ is hydrogen, halo, methyl or mono-, di- or tri-halomethyl;

R is

wherein
$Z^2$ is S; and
$R^A$ is $R^{10}$—W— wherein
W is O; and
$R^{10}$ is a linear or branched, unsubstituted or halo-substituted $C_1$–$C_8$ alkyl, $C_2$–$C_8$ alkenyl, $C_2$–$C_8$ alkynyl; a $C_3$–$C_7$ cycloalkyl, $C_3$–$C_7$ cycloalkyl $C_1$–$C_6$ alkyl, $C_3$–$C_7$ cycloalkenyl unsubstituted or substituted by $C_1$–$C_6$ alkyl; an unsubstituted phenyl or phenyl substituted by halo, $C_1$-$C_6$ alkyl, $C_1$-$C_6$ alkoxy, carboxyl, $C_1$-$C_8$ haloalkyl, $C_3$-$C_7$ cycloalkyl, $C_1$-$C_8$ alkylthio, phenyl, nitro, amino, hydroxyl, acetyl acetyloxy, phenoxy, $C_1$-$C_8$ alkoxycarbonyl, $C_1$-$C_8$ alkylcarbonyl.

2. A compound having the formula:

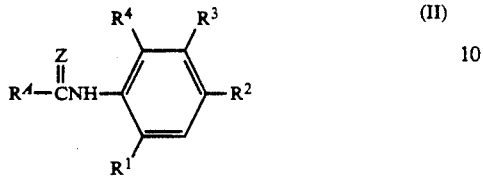

(II)

wherein

Z is S;

$R^4$ is a $C_1$-$C_8$ alkoxy; a $C_2$-$C_8$ alkenyloxy; a $C_2$-$C_8$ alkynyloxy; a $C_3$-$C_8$ cycloalkyloxy; a $C_3$-$C_8$ cycloalkyl- alkoxy; a $C_7$-$C_8$ phenoxyalkyl or a phenoxy;

$R^1$ is hydrogen, halogen, $C_1$-$C_4$ alkyl or $C_1$-$C_4$ alkoxy;

$R^2$ is hydrogen, halogen, $C_1$-$C_4$ alkyl, $C_1$-$C_4$ alkoxy, hydroxy, mono-, di- or tri-halomethyl, trifluoromethoxy, methylthio, nitro, cyano, acetoxy or dimethylamino;

$R^3$ is —$CO_2R^5$ wherein $R^5$ is an alkyl, a $C_3$-$C_6$ alkenyl or alkynyl, a one to six haloalkyl, an alkoxyalkyl, an alkylthioalkyl, a carboxyalkyl, an alkylcarboxyalkyl, a $C_6$-$C_{12}$ arylcarboxyalkyl, an alkylaminoalkyl or dialkylaminoalkyl, a trialkylsilylalkyl, each of the aforementioned alkyl moieties having from one to eight carbon atoms; a phenyl, a naphthyl, a $C_1$-$C_6$ alkylphenyl, a $C_7$-$C_{12}$ arylalkyl or alkarylalkyl, a $C_3$-$C_8$ carbocyclyl, a $C_1$-$C_4$ alkyl $C_3$-$C_8$ carbocyclyl;

$R^4$ is hydrogen, halo, methyl or mono-, di- or trihalomethyl.

3. A compound according to claim 1 wherein said compound has the formula:

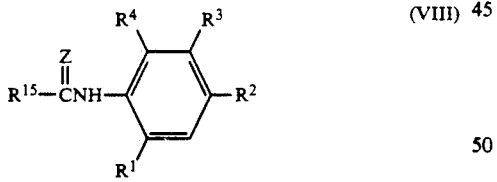

(VIII)

wherein $R^{15}$ is a $C_1$-$C_8$ alkoxy; a $C_2$-$C_8$ alkenyloxy or alkynyloxy; a $C_1$-$C_8$ aryloxy; a $C_3$-$C_8$ cycloalkyloxy, cycloalkylalkyloxy, cycloalkylaryloxy;

Z is S;

$R^1$ is hydrogen, halo or $C_1$-$C_4$ alkyl or $C_1$-$C_4$ alkoxy;

$R^2$ is hydrogen, halogen, $C_1$-$C_4$ alkyl, $C_1$-$C_4$ alkoxy, hydroxy, mono-, di- or tri-halomethyl, trifluoromethoxy, methylthio, nitro, cyano, acetoxy or dimethylamino;

$R^3$ is —$CO_2R^5$ wherein $R^5$ is an alkyl, a $C_3$-$C_6$ alkenyl or alkynyl, a one to six haloalkyl, an alkoxyalkyl, an alkylthioalkyl, a carboxyalkyl, an alkylcarboxyalkyl, a $C_6$-$C_{12}$ arylcarboxyalkyl, an alkylaminoalkyl or dialkylaminoalkyl, a trialkylsilylalkyl, each of the aforementioned alkyl moieties having from one to eight carbon atoms; a phenyl, a naphthyl, a $C_1$-$C_6$ alkylphenyl, a $C_7$-$C_{12}$ arylalkyl or alkarylalkyl, a $C_3$-$C_8$ carbocyclyl, a $C_1$-$C_4$ alkyl $C_3$-$C_8$ carbocyclyl;

$R^4$ is hydrogen, halo, methyl or mono-, di- or trihalomethyl.

4. A compound according to claim 3 wherein $R^1$ is hydrogen or a fluoro;

$R^4$ is hydrogen; and $R^{15}$ is a $C_1$-$C_8$ alkoxy; a $C_2$-$C_8$ alkenyloxy or alkynyloxy; phenoxy; $C_3$-$C_8$ cycloalkoxy or cycloalkylalkyloxy; cycloalkylphenyloxy.

5. A compound of claim 1 wherein said compound is selected from the group consisting of:

(1) 1-methylethyl 2-chloro-5-[[(1-methylethoxy)thioxomethyl]amino]benzoate;

(2) 1-methylethyl 2-chloro-5-[(ethoxythioxomethyl)amino]benzoate;

(3) 1-methylethyl 5-[(butoxythioxomethyl)amino]2-chlorobenzoate;

(4) 1-methylethyl 2-chloro-5-[(propoxythioxomethyl)amino]benzoate;

(5) 1-methylethyl 2-chloro-5-[[(pentyloxy)thioxomethyl]amino]benzoate;

(6) 1-methylethyl 2-chloro-5-[[(2-propenyloxy)thioxomethyl]amino]benzoate;

(7) 1-methylethyl 2-chloro-5-[[(2-cyclohexen-1-yloxy)thioxomethyl]amino]benzoate;

(8) 1-methylethyl 2-chloro-5-[[(cyclohexyloxy)thioxomethyl]amino]benzoate;

(9) 1-methylethyl 2-chloro-5-[[(cyclopropylmethoxy)thioxomethyl]amino]benzoate; and

(10) 1-methylethyl 2-chloro-5-[[(2-methoxyethoxy)-thioxomethyl]amino]benzoate.

6. The intermediate compound 2-chloro-5-[[(1-methylethoxy)thioxomethyl]amino]benzoic acid.

7. A compound of claim 5 wherein said compound is 1-methylethyl 2-chloro-5-[[(1-methylethoxy)thioxomethyl]amino]benzoate.

8. A pharmaceutical formulation for inhibiting the growth or replication of HIV which comprises an effective amount of the compound of claim 1 in a pharmaceutically acceptable carrier.

* * * * *

UNITED STATES PATENT AND TRADEMARK OFFICE
CERTIFICATE OF CORRECTION

PATENT NO. : 5,268,389

DATED : December 7, 1993

INVENTOR(S) : Harrison et al

It is certified that error appears in the above-identified patent and that said Letters Patent is hereby corrected as shown below:

In column 14, lines 40 - 45

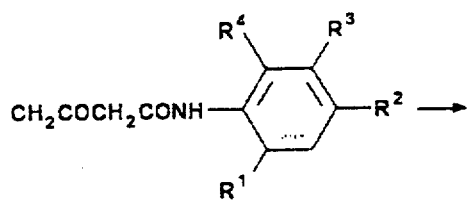

should read:

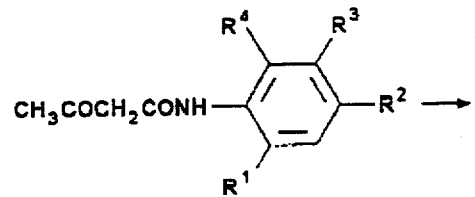

UNITED STATES PATENT AND TRADEMARK OFFICE
CERTIFICATE OF CORRECTION

PATENT NO. : 5,268,389

DATED : December 7, 1993

INVENTOR(S) : Harrison et al

It is certified that error appears in the above-identified patent and that said Letters Patent is hereby corrected as shown below:

In column 14, lines 45-50

``
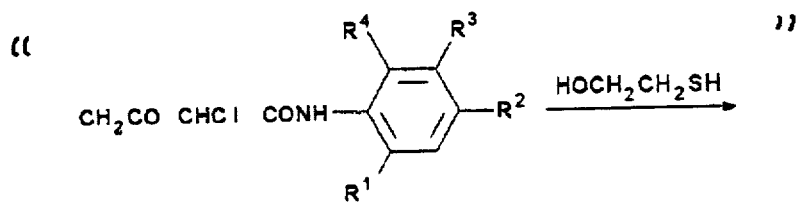
'' should read

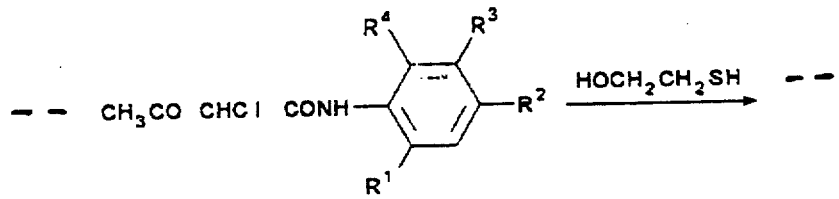

UNITED STATES PATENT AND TRADEMARK OFFICE
CERTIFICATE OF CORRECTION

PATENT NO. : 5,268,389

DATED : December 7, 1993

INVENTOR(S) : Harrison et al

It is certified that error appears in the above-identified patent and that said Letters Patent is hereby corrected as shown below:

In column 14, lines 55-60

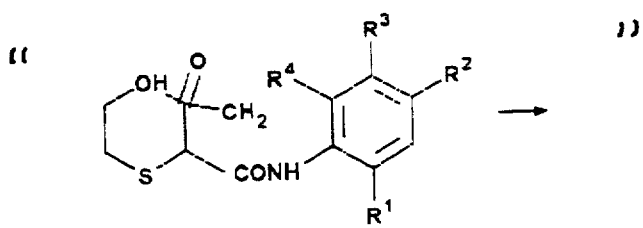

should read

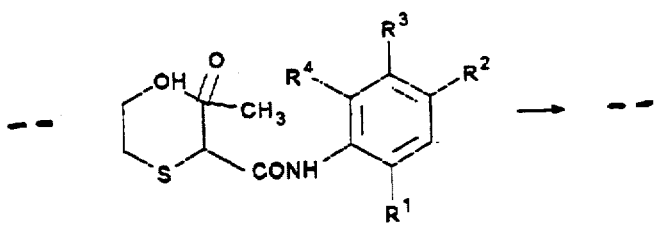

UNITED STATES PATENT AND TRADEMARK OFFICE
CERTIFICATE OF CORRECTION

PATENT NO. : 5,268,389

DATED : December 7, 1993

INVENTOR(S) : Harrison et al

It is certified that error appears in the above-identified patent and that said Letters Patent is hereby corrected as shown below:

In column 14, lines 60-65

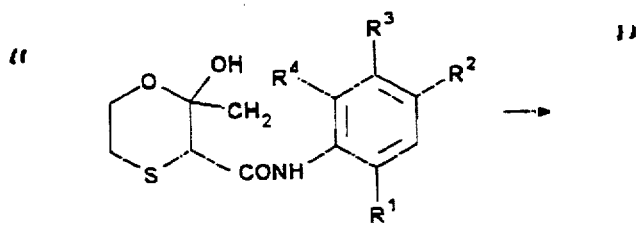

should read

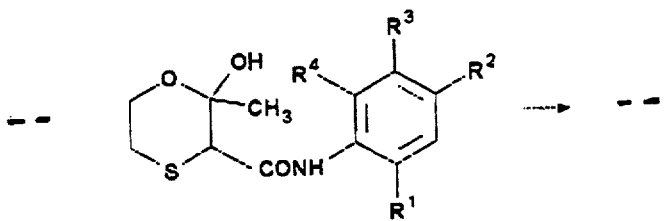

UNITED STATES PATENT AND TRADEMARK OFFICE
CERTIFICATE OF CORRECTION

PATENT NO. : 5,268,389
DATED : December 7, 1993
INVENTOR(S) : Harrison et al

It is certified that error appears in the above-identified patent and that said Letters Patent is hereby corrected as shown below:

In claim 1, lines 54-60:

"R is

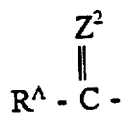

wherein . . ."

should read:

--R is $R^z$ - NH - wherein $R^z$ is

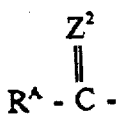

wherein . . .--.

UNITED STATES PATENT AND TRADEMARK OFFICE
CERTIFICATE OF CORRECTION

PATENT NO. : 5,268,389

DATED : December 7, 1993

INVENTOR(S) : Harrison et al

It is certified that error appears in the above-identified patent and that said Letters Patent is hereby corrected as shown below:

In column 8, lines 35-40

" 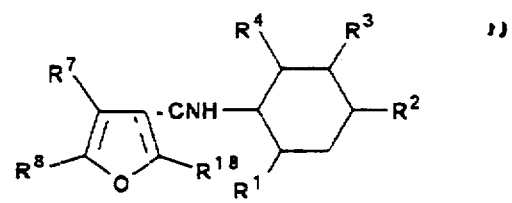 "

should read:

-- 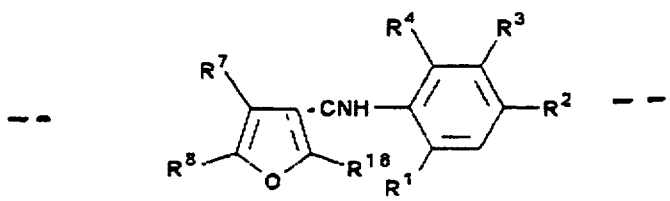 --

UNITED STATES PATENT AND TRADEMARK OFFICE
CERTIFICATE OF CORRECTION

PATENT NO.   :   5,268,389

DATED        :   December 7, 1993

INVENTOR(S)  :   Harrison et al

It is certified that error appears in the above-identified patent and that said Letters Patent is hereby corrected as shown below:

In column 23, Table 1, the formula for $R^{14}$ of compound 114 "NH COCN$_3$,", should read --NHCOCH$_3$--.

In column 30, the structure of compound 94

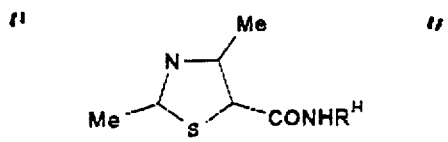

should read

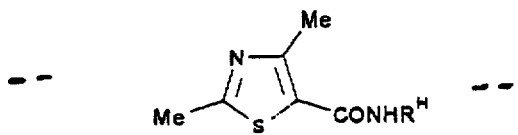

UNITED STATES PATENT AND TRADEMARK OFFICE
CERTIFICATE OF CORRECTION

PATENT NO. : 5,268,389

DATED : December 7, 1993

INVENTOR(S) : Harrison et al

It is certified that error appears in the above-identified patent and that said Letters Patent is hereby corrected as shown below:

In column 30, the structure of compound 98

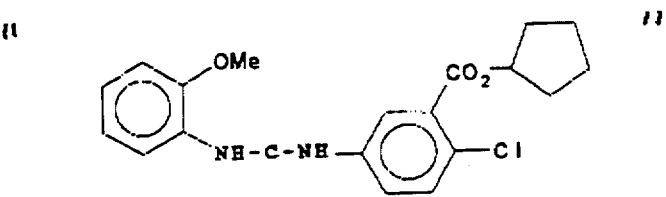

should read:

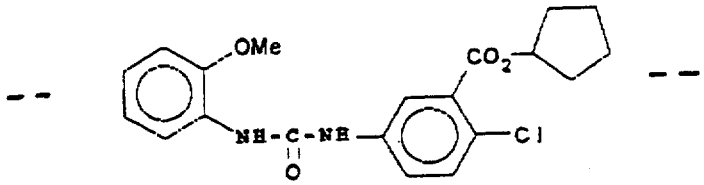

UNITED STATES PATENT AND TRADEMARK OFFICE
CERTIFICATE OF CORRECTION

PATENT NO. : 5,268,389

DATED : December 7, 1993

INVENTOR(S) : Harrison et al

It is certified that error appears in the above-identified patent and that said Letters Patent is hereby corrected as shown below:

In column 16, line 35, "R^OH", should read --R^NH--.

In column 23, Table 1:

"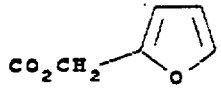"

should read:

-- 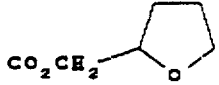 --

UNITED STATES PATENT AND TRADEMARK OFFICE
CERTIFICATE OF CORRECTION

PATENT NO. : 5,268,389
DATED : December 7, 1993
INVENTOR(S) : Harrison, et al.

It is certified that error appears in the above-indentified patent and that said Letters Patent is hereby corrected as shown below:

In column 16, line 35, "R^OH", should read --R^NH--.

In column 23, Table 1:

"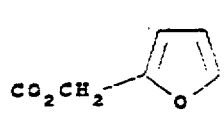"

UNITED STATES PATENT AND TRADEMARK OFFICE
CERTIFICATE OF CORRECTION

PATENT NO. : 5,268,389
DATED : December 7, 1993
INVENTOR(S) : Harrison, et al.

It is certified that error appears in the above-indentified patent and that said Letters Patent is hereby corrected as shown below:

should read:

Signed and Sealed this

Thirteenth Day of December, 1994

Attest:

BRUCE LEHMAN

Attesting Officer    Commissioner of Patents and Trademarks